(12) United States Patent
Min

(10) Patent No.: US 9,314,634 B2
(45) Date of Patent: Apr. 19, 2016

(54) INITIATION TESTS AND GUIDELINES FOR IMPLEMENTING CARDIAC THERAPY

(75) Inventor: Xiaoyi Min, Thousand Oaks, CA (US)

(73) Assignee: Pacesetter, Inc., Sylmar, CA (US)

(*) Notice: Subject to any disclaimer, the term of this patent is extended or adjusted under 35 U.S.C. 154(b) by 1271 days.

(21) Appl. No.: 12/264,077

(22) Filed: Nov. 3, 2008

(65) Prior Publication Data

US 2010/0114232 A1    May 6, 2010

(51) Int. Cl.
*A61N 1/362* (2006.01)
*A61N 1/372* (2006.01)

(52) U.S. Cl.
CPC .......... *A61N 1/3627* (2013.01); *A61N 1/37247* (2013.01)

(58) Field of Classification Search
CPC .......... A61N 1/3627; A61N 1/37247
USPC ......... 607/2, 9, 14, 17, 19, 30, 59, 31, 4–5; 600/301, 508, 515, 522, 529; 128/898; 705/2–3; 382/128
See application file for complete search history.

(56) References Cited

U.S. PATENT DOCUMENTS

| | | | |
|---|---|---|---|
| 4,712,555 A | 12/1987 | Thornander et al. | |
| 4,788,980 A | 12/1988 | Mann et al. | |
| 4,940,052 A | 7/1990 | Mann et al. | |
| 5,466,254 A | 11/1995 | Helland | |
| 5,476,483 A | 12/1995 | Bornzin et al. | |
| 6,314,323 B1 | 11/2001 | Ekwall | |
| 2004/0082888 A1* | 4/2004 | Palazzolo et al. | 601/41 |
| 2005/0209650 A1* | 9/2005 | Van Gelder et al. | 607/25 |
| 2006/0229679 A1* | 10/2006 | Joo | 607/5 |
| 2007/0156179 A1* | 7/2007 | Karashurov | 607/2 |
| 2007/0191901 A1* | 8/2007 | Schecter | 607/17 |
| 2008/0058656 A1* | 3/2008 | Costello et al. | 600/508 |
| 2008/0097536 A1* | 4/2008 | Kramer et al. | 607/9 |
| 2008/0103533 A1* | 5/2008 | Patel et al. | 607/2 |
| 2008/0255629 A1* | 10/2008 | Jenson et al. | 607/19 |
| 2009/0036769 A1* | 2/2009 | Zdeblick | 600/424 |
| 2009/0234240 A1* | 9/2009 | Kuenzler et al. | 600/529 |
| 2010/0023078 A1* | 1/2010 | Dong et al. | 607/9 |
| 2010/0087745 A1* | 4/2010 | Fischell et al. | 600/515 |
| 2010/0331854 A1* | 12/2010 | Greenberg et al. | 606/129 |

* cited by examiner

*Primary Examiner* — Catherine Voorhees

(57) ABSTRACT

An exemplary system includes a programmer configured to instruct an implantable device and a qualification module with instructions to call for tests performed by an implantable device configured for delivery of CRT, to receive results from the tests, to analyze the results and to decide, based on the analysis, if the patient qualifies for automatic, implantable device-based optimization of one or more CRT parameters and, only if the patient qualifies for automatic, implantable device-based optimization of one or more CRT parameters, presenting a graphical user interface that comprises a selectable control to enable an algorithm of an implantable device to automatically optimize at least one of the one or more cardiac resynchronization therapy parameters. Other exemplary methods, devices, systems, etc., are also disclosed.

10 Claims, 16 Drawing Sheets

INITIATION TESTS AND GUIDELINES FOR IMPLEMENTING CARDIAC THERAPY

TECHNICAL FIELD

Exemplary techniques presented herein generally relate to cardiac therapy. Various exemplary techniques assess patient information and determine options for implementing cardiac therapy.

BACKGROUND

Cardiac resynchronization therapy (CRT) can increase quality of life by improving cardiac performance. Most CRTs rely on a set of parameters that can be optimized according to various criteria. As cardiac conditions change, for better or worse, such parameters may be periodically re-optimized. In general, benefits of CRT increase with frequency of optimization. However, certain cardiac conditions can confound optimization or otherwise make optimization problematic. For example, atrial fibrillation (AF), which often occurs in conjunction with congestive heart failure (CHF), can confound measurement of some delays used in the QuickOpt™ optimization algorithm (St. Jude Medical, Inc., Sylmar, Calif.).

To account for such cardiac conditions, clinicians must understand thoroughly how optimization algorithms function and carefully assess patient information prior to implementing CRT and/or optimization algorithms for CRT parameters. Various exemplary techniques described herein provide a framework to guide clinicians in making such decisions and to manually or automatically implement specialized features to account for particular cardiac conditions.

SUMMARY

An exemplary system includes a programmer configured to instruct an implantable device and a qualification module with instructions to call for tests performed by an implantable device configured for delivery of CRT, to receive results from the tests, to analyze the results and to decide, based on the analysis, if the patient qualifies for automatic, implantable device-based optimization of one or more CRT parameters and, only if the patient qualifies for automatic, implantable device-based optimization of one or more CRT parameters, presenting a graphical user interface that comprises a selectable control to enable an algorithm of an implantable device to automatically optimize at least one of the one or more cardiac resynchronization therapy parameters.

In general, the various devices, methods, etc., described herein, and equivalents thereof, are suitable for use in a variety of pacing therapies and other cardiac related therapies.

BRIEF DESCRIPTION OF THE DRAWINGS

Features and advantages of the described implementations can be more readily understood by reference to the following description taken in conjunction with the accompanying drawings.

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators generally reference like parts or elements.

Overview

As described herein, an implantable device can deliver cardiac resynchronization therapy (CRT) according to one or more programmable parameters. Such parameters are typically programmed by a clinician using a programmer, which is a computing device configured to communicate with an implantable device. For example, a patient may be required to visit a clinic periodically for a procedure that involves a clinician placing a programmer's telemetric wand in proximity to the patient's implanted cardiac therapy device to thereby acquire information from the implantable device, instruct the implantable device to perform a test or tests and optionally set one or more parameters germane to how the implantable device functions. In this example, between clinic visits, conditions may change such that one or more parameters are suboptimal. For an implantable device with a built-in optimization algorithm, a clinician may enable this algorithm. Various exemplary techniques described herein pertain to such optimization algorithms (e.g., criteria to enable and mechanisms to enable an optimization algorithm).

Exemplary Stimulation Device

The techniques described below are intended to be implemented in connection with any stimulation device that is configured or configurable to stimulate nerves and/or stimulate and/or shock a patient's heart.

Figure 1:
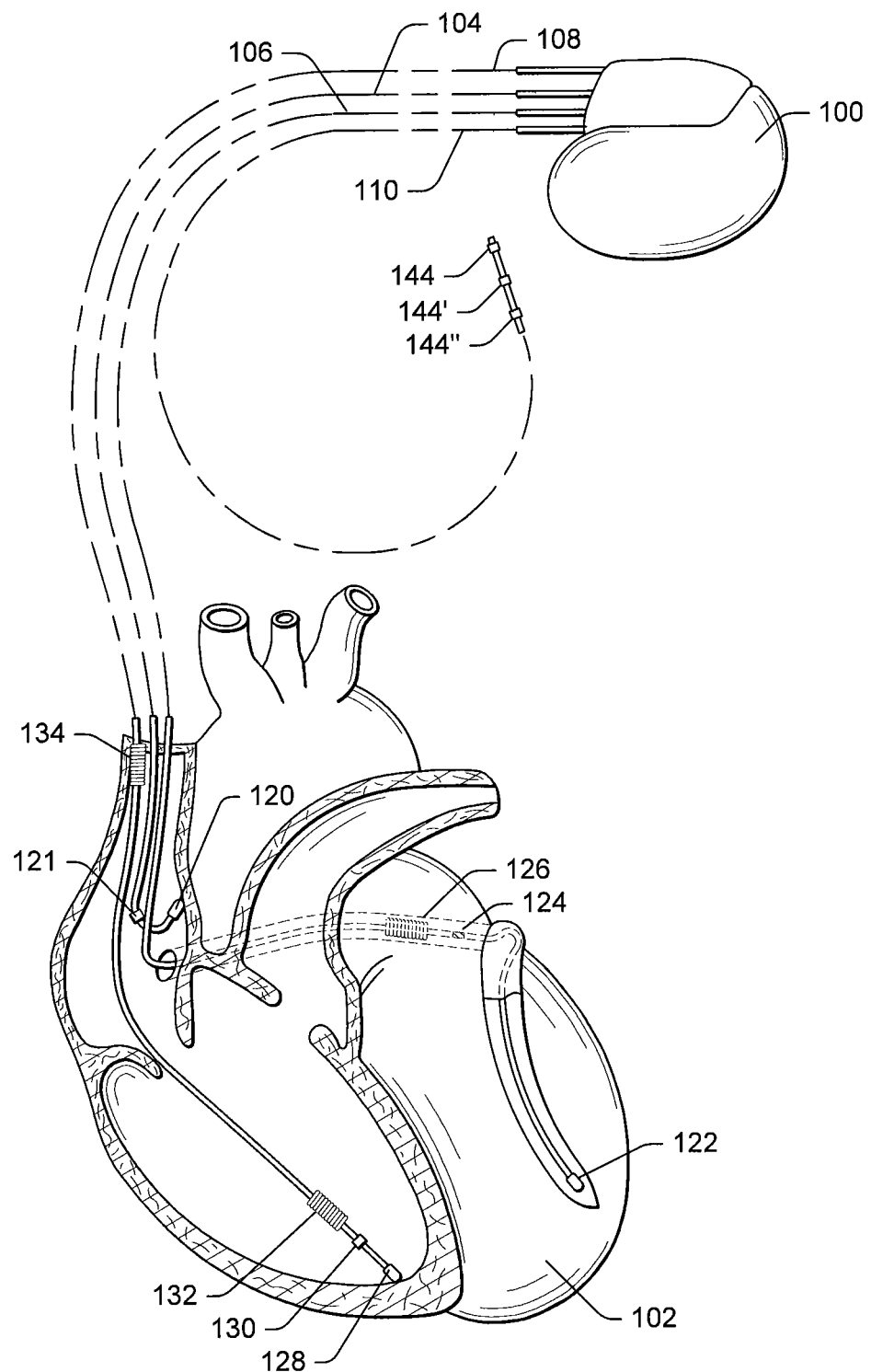
FIG. 1 is a simplified diagram illustrating an exemplary implantable stimulation device in electrical communication with various leads implanted into a patient's heart.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves, non-myocardial tissue, other nerves, etc. In addition, the device 100 includes a fourth lead 110 having, in this implementation, three electrodes 144, 144', 144" suitable for stimulation of autonomic nerves, non-myocardial tissue, other nerves, etc. For example, this lead may be positioned in and/or near a patient's heart or near an autonomic nerve within a patient's body and remote from the heart.

The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves, non-myocardial tissue, other nerves, etc.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, non-myocardial tissue, other nerves, etc., wherein such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, non-myocardial tissue, other nerves, etc., wherein such an electrode may be positioned on the lead or a bifurcation or leg of the lead.

Figure 2:
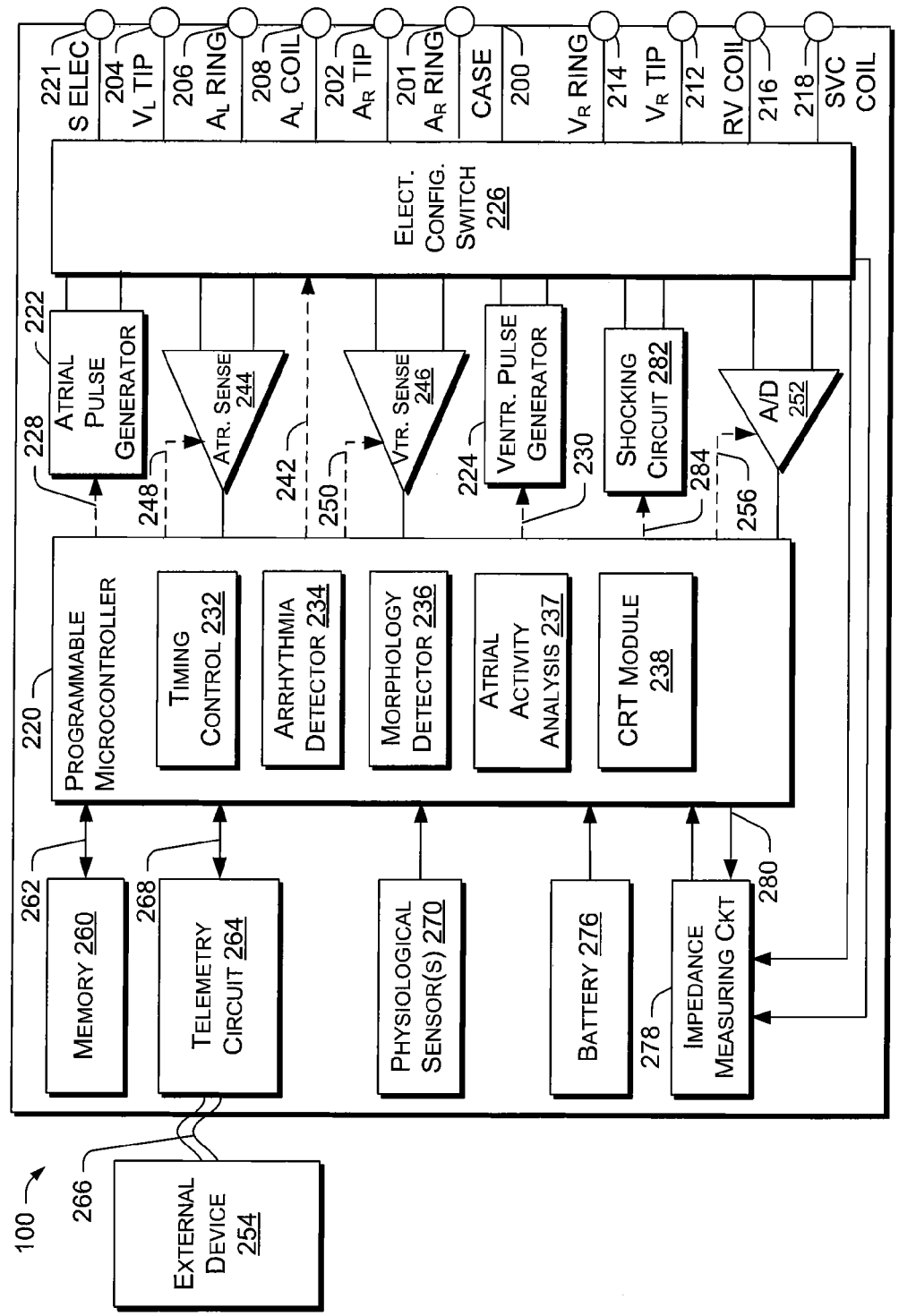
FIG. 2 is a functional block diagram of an exemplary implantable stimulation device illustrating basic elements that are configured to provide cardioversion, defibrillation, pacing stimulation and/or other tissue and/or nerve stimulation. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves, non-myocardial tissue, other nerves, etc. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, autonomic nerve stimulation, non-myocardial tissue stimulation, other nerve stimulation, etc.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing and/or pacing, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing and/or shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

To support right chamber sensing, pacing, and/or shocking, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular delay (AV or more specifically $AV_{RV}$ or $AV_{LV}$), atrial interconduction delay (e.g., A–A or more specifically $A_R$–$A_L$ or $A_L$–$A_R$), or ventricular interconduction delay (VV or more specifically $V_{LV}$–$V_{RV}$ or $V_{RV}$–$V_{LV}$), etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes an atrial activity analysis module 237. The atrial activity analysis module 237 optionally implements one or more methods for sensing, information analysis, and/or stimulation control related to atrial activity. For example, the atrial activity analysis module 237 optionally implements one or more of the exemplary methods described below.

Microcontroller 220 further includes a cardiac resynchronization therapy (CRT) module 238 for performing a variety of tasks related to CRT. For example, the CRT module 238 may implement a therapy that relies on pacing a ventricle or pacing both ventricles to promote mechanical synchrony and cardiac performance. The CRT module 238 may be implemented in hardware as part of the microcontroller 220, or as software/firmware instructions programmed into the device and executed on the microcontroller 220 during certain modes of operation. The CRT module 238 may optionally implement various exemplary methods described herein.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or a data acquisition system 252 (e.g., where the microcontroller 220 can control the A/D converter 252 by way of a control signal 256) to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation) are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) to determine a type of remedial therapy, if so desired (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve or other tissue stimulation lead 110 through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms (IEGMs) and status information relating to the operation of the device 100 (as contained in the microcontroller 220 or memory 260) to be sent to the external device 254 through an established communication link 266.

The stimulation device 100 can further include one or more physiologic sensors 270. For example, a physiologic sensor may be a "rate-responsive" sensor used to adjust pacing stimulation rate according to activity state of a patient. The one or more physiological sensors 270 may include a sensor to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AA delay, AV delay, VV delay, etc.) at which the atrial and ventricular pulse generators, 222 and 224, generate stimulation pulses.

While shown as being included within the stimulation device 100, it is to be understood that a physiologic sensor may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, hemodynamics, pressure, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

The one or more physiological sensors 270 optionally include a minute ventilation sensor (e.g., where minute ventilation is defined as the total volume of air that moves in and out of a patient's lungs in a minute). Signals generated by a sensor can be passed to the microcontroller 220 for analysis in determining whether to adjust the pacing rate, etc. In various configurations, the microcontroller 220 monitors signals for indications of activity status. Where a device includes a position sensor (e.g., accelerometer), the device may determine, for example, whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Figure 3:
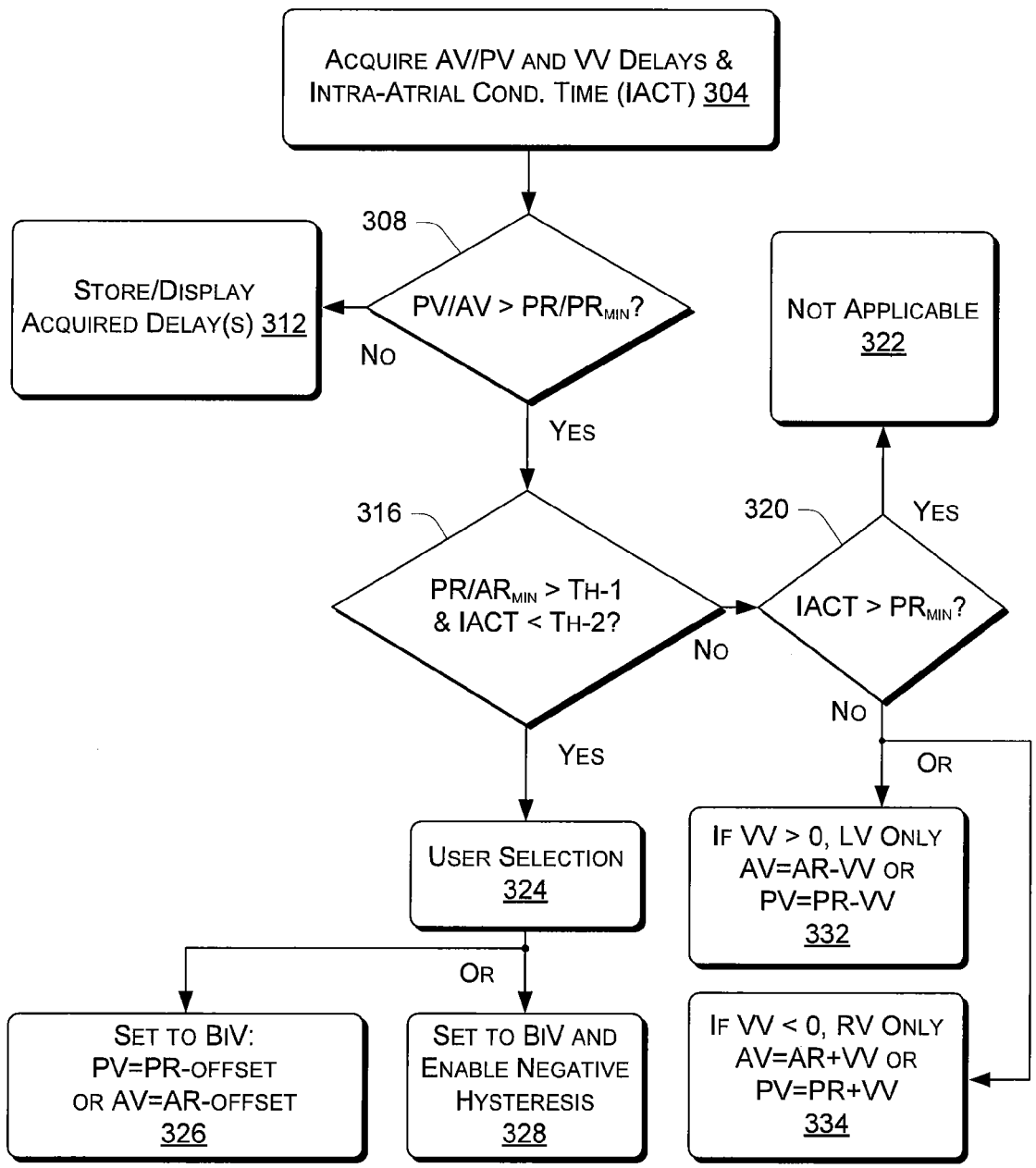
FIG. 3 is a block diagram of a programmer-based method that allows a user to program an implantable stimulation device to deliver cardiac resynchronization therapy (CRT).

FIG. 3 shows a method 300 for interacting with an implantable device (e.g., via a device programmer) to acquire information, to perform one or more tests and optionally enable one or more pacing algorithms. In the example of FIG. 3, the method 300 commences in an acquisition block 304 where a programmer acquires various values from memory of an implantable device such as the device 100 of FIGS. 1 and 2. Where a value is not readily available or not current, the programmer may instruct the implantable device to make measurements, determinations, etc., to provide a value.

In FIG. 3, the acquisition block 304 shows parameters, or measures, AV delay, PV delay, VV delay and intra-atrial conduction time (noting that a P-wave or A-wave width ($\Delta P$ and $\Delta A$) may be an indicator intra-atrial conduction time). Given the acquired value or values, various decisions follow, according to a decision algorithm executed by the programmer. For example, the programmer may include an algorithm with a first decision block 308 that decides whether the acquired PV delay or AV delay exceeds a minimum value ($PR_{min}$ or $AR_{min}$). If the decision block 308 decides that the delay does not exceed the minimum value, the method 300 terminates in a block 312 that may simply store or display the acquired delay or delays. However, if the decision block 308 decides that the acquired PV delay or AV delay exceeds the minimum value ($PR_{min}$ or $AR_{min}$), then the method 300 continues at another decision block 316 that decides if the minimum value is greater than a predetermined threshold (Th-1) and if the IACT is less than another predetermined threshold (Th-2).

The decision block 316 continues at yet another decision block 320 if the conditions are not met and continues at a user selection block 324 if the conditions are met. If the conditions are not met, the decision block 320 decides if the acquired IACT exceeds a minimum PR delay. If it does, then the method 300 continues at a "not applicable" block 322 to indicate other techniques may be required to properly set one or more parameters of the implantable device. However, if the decision block 320 decides that IACT does not exceed the minimum PR delay, the method 300 continues with single ventricle pacing. For example, if the VV delay exceeds zero then per a determination block 332, pacing occurs in the left ventricle (and not in the right ventricle); whereas, if the VV delay is less than zero, then per a determination block 334, pacing occurs in the right ventricle (and not in the left ventricle).

Referring again to the user selection block 324, where conditions of the decision block 316 have been met, a programmer may display options for a clinician as to how to program a patient's implantable device. In the example of FIG. 3, two options are shown: per an option block 326, set to bi-ventricular pacing using an offset measure; or, per an option block 328, set to bi-ventricular pacing with negative hysteresis enabled. The negative hysteresis option relies on an algorithm that aims to ensure pacing (e.g., to adjust AV delay or PV delay to be less than an intrinsic conduction interval AR or PR).

As described herein, an exemplary method may include various steps of the method 300 of FIG. 3 while optionally providing for implantable device-based optimization of one or more parameters. Such device-based optimization can allow for periodic adjustments to a patient's therapy (e.g., between clinic visits).

Figure 4:
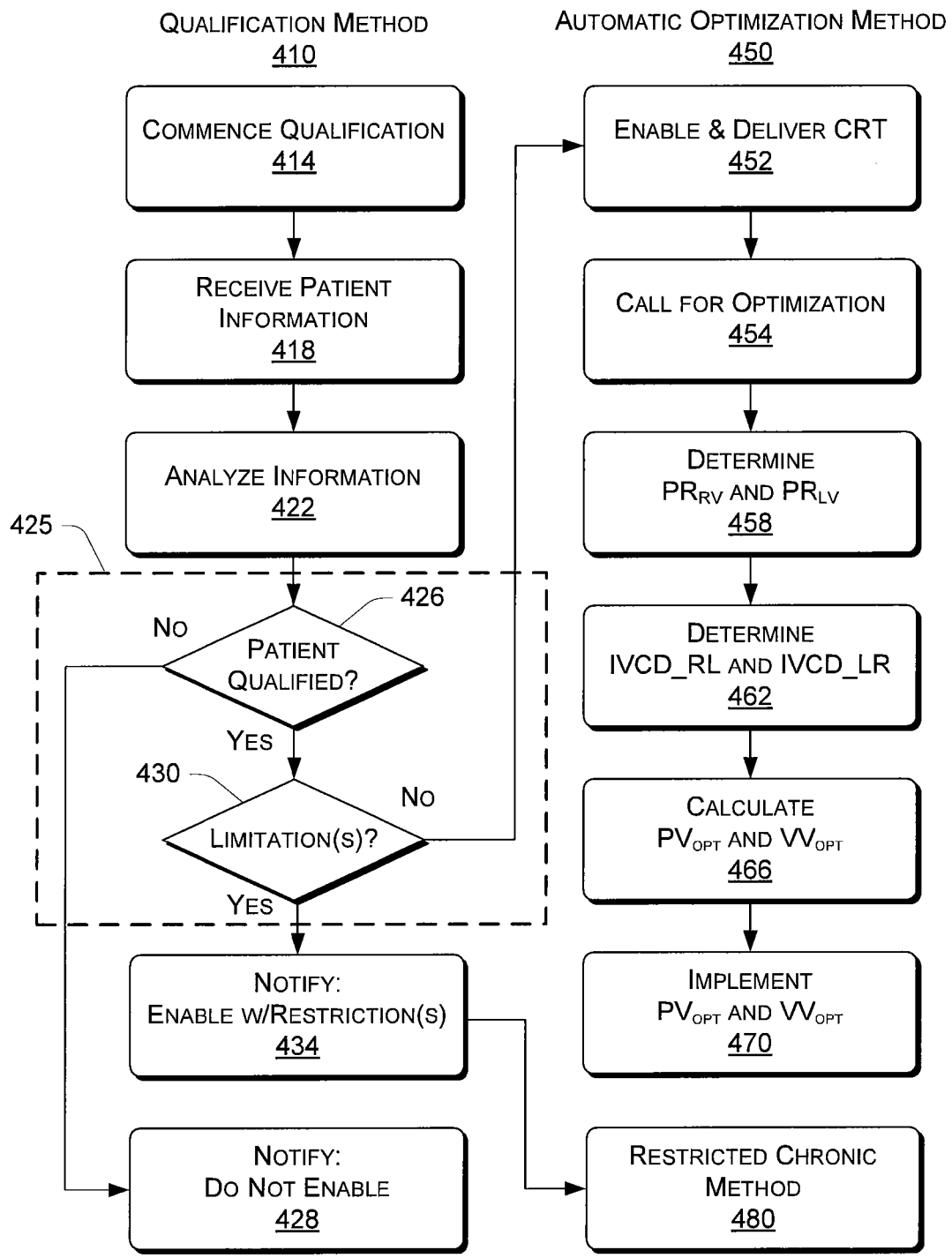
FIG. 4 is a block diagram of an exemplary method for qualifying a patient for CRT and a method for automatically optimizing one or more CRT parameters.

FIG. 4 shows an exemplary method 410 for qualifying a patient for CRT and an example of an automatic optimization method 450 for CRT. The qualification method 410 commences in a commencement block 414. For example, a clinician may start a program (e.g., an application) on a computing device where the computing device is in communication with one or more networks. In a reception block 418, the device receives patient information. An analysis block 422 follows where the program analyzes the patient information. For example, an exemplary program may analyze patient information with respect to requirements of one or more CRT algorithms. A decision block 426 decides whether a patient is, in general, qualified for CRT.

If the decision block 426 decides that the patient is not qualified for CRT, then the program indicates in a notification block 428 that CRT algorithms should not be enabled. The aforementioned computing device may include circuitry for communication with an implantable device and may communicate with the implantable device to ensure that CRT algorithms are not enabled.

If the decision block 426 decides that the patient is, in general, qualified for CRT, then the method 410 continues at another decision block 430. The decision block 430 assesses patient information to decide if one or more limitations exist that may confound one or more aspects of CRT. For example, a patient may be qualified, in general, yet have a condition that confounds a particular optimization algorithm for optimizing one or more CRT parameters. If the decision block 430 decides that one or more limitations exist for the patient, then the method 410 proceeds to a notification block 434 that notifies the clinician that CRT may be enabled with one or more restrictions. A restricted chronic CRT method may be enabled per block 480.

Referring again to the decision block 430, if no limitations exist, then the method 410 may proceed to an enablement block 452 to enable and deliver CRT. For example, the aforementioned computing device may communicate instructions to an implantable CRT device that call for delivery of CRT where one or more CRT optimization algorithms execute to optimize delivery of the CRT.

In the example of FIG. 4, the method 450 delivers CRT with periodic optimization according to a specific set of algorithms. A call block 454 calls for optimization according to a schedule, a signal, a cardiac condition, etc. As part of the optimization procedure, a determination block 458 determines a $PR_{RV}$ interval and a $PR_{LV}$ interval while another determination block 462 determines an interventricular conduction delay from the right ventricle to the left ventricle (IVCD_RL) and an interventricular conduction delay from the left ventricle to the right ventricle (IVCD_LR). In general, to determine IVCD_RL or IVCD_LR a stimulus is delivered to one ventricle and a conducted wavefront is sensed in the other ventricle. Such an IVCD may be referred to as a paced IVCD. Alternatively, a sensed IVCD may be used where an intrinsic event is sensed in one ventricle and a conducted wavefront associated with the sensed intrinsic event is sensed in the other ventricle. In either instance, the IVCD provides information about directional conduction between the ventricles.

According to the method 450, a determination block 466 relies on the measured PRRV, PRLV, IVCD_RL and IVCD_LR values to determine an optimum PV delay ($PV_{Opt}$) and an optimum VV delay ($VV_{Opt}$). An implementation block 470 implements the optimized delays $PV_{Opt}$ and $VV_{Opt}$.

As may be appreciated, if the determination block 458 cannot measure or otherwise determine $PR_{RV}$ or $PR_{LV}$, the calculation block 466 may not be able to calculate $PV_{Opt}$ and/or $VV_{Opt}$. Similarly, if the determination block 462 cannot accurately measure or otherwise determine IVCD_RL or IVCD_LR, the calculation block 466 may not function or function improperly. As described herein, various cardiac conditions can confound measurements such as those required for the measures presented in determination blocks 458 and 462. In some instances, one or more alternative algorithms or techniques are available to estimate these measures or to optimize $PV_{Opt}$ and/or $VV_{Opt}$. Consequently, a patient may be able to benefit from a "restricted" or alternative method to optimize one or more CRT parameters (e.g., per the restricted chronic method 480).

Figure 5:
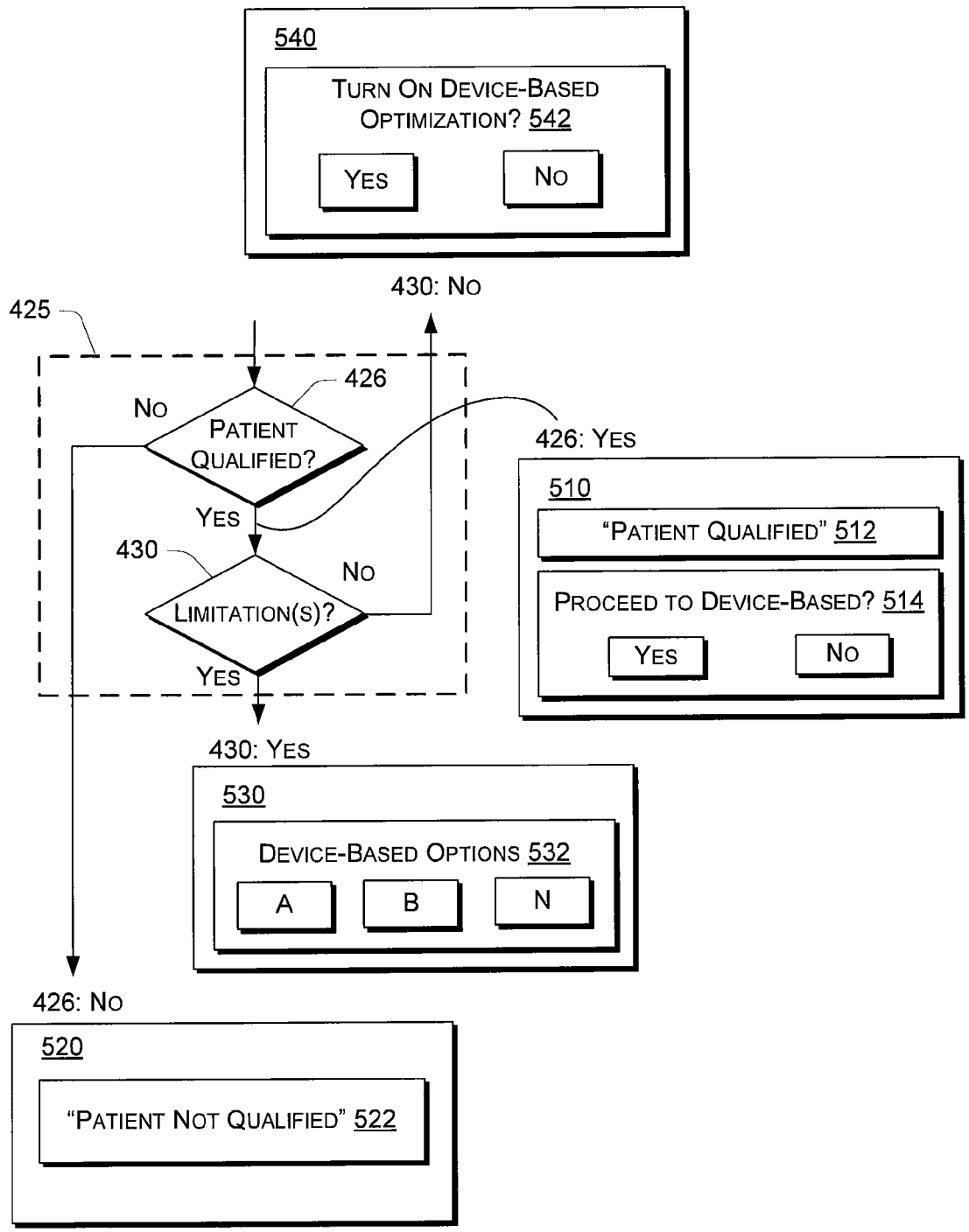
FIG. 5 is a block diagram of two decision steps of FIG. 3 and exemplary graphical user interfaces (GUI) for guiding a clinician.

FIG. 5 shows various exemplary graphical user interfaces (GUIs) in association with decisions of the decision tree 425 of FIG. 4 (e.g., per the decision blocks 426 and 430). The GUIs aim to reduce risk associated with implementation of implantable device-based optimization of one or more parameters germane to CRT (e.g., PV delay, AV delay or VV delay). Specifically, in the example of FIG. 5, if a patient is not qualified for device-based optimization, a programmer will not display a user interface control that allows for implementation of device-based optimization.

As explained with respect to FIG. 4, the decision block 426 has a "No" state and a "Yes" state. For the "No" state, a user interface 520 has a field 522 that indicates the patient is not qualified for implantable device-based optimization for one or more parameters germane to CRT. Further, the user interface 520 does not provide an option to enable implantable device-based optimization. Along this decision path (i.e., the "No" state), the absence of a control to enable implantable device-based optimization for CRT reduces risk.

In contrast to the user interface 520, a user interface 510 associated with the "Yes" state of the decision block 426 includes a selectable control field 514 that allows a user to directly or indirectly (see, e.g., user interfaces 530 and 540) enable implantable device-based optimization for CRT. In the example of FIG. 5, the user interface 510 further includes a field 512 that indicates a patient is qualified for implantable device-based optimization for CRT. Such a field is optional as display of the selectable control field 514 inherently indicates that a patient is qualified.

An exemplary method may include the decision block 426 and user interfaces 510 and 520 without the decision block 430. However, in the example of FIG. 5 (and FIG. 4), the analysis block 422 can determine whether a patient is qualified with certain limitations or restrictions (see, e.g., notification block 434 of FIG. 4). For the "No" state of the "limitations" decision block 430, the user interface 540 includes a selectable control field 542 to allow a clinician to "turn on device-based optimization"; whereas, for the "Yes" state, the user interface 530 includes one or more selectable control fields 532 that allow a clinician to select a form of implantable device-based optimization that can operate given one or more limitations.

With respect to measures and parameters used in optimization or delivery of a cardiac therapy (e.g., cardiac resynchronization therapy), these may include:

| | |
|---|---|
| PP, AA | Interval between successive atrial events |
| IACT | Intra-atrial conduction time (see also ΔP, ΔA) |
| PV | Delay between an atrial event and a paced ventricular event |
| $PV_{optimal}$ | Optimal PV delay |
| $PV_{RV}$ | PV delay for right ventricle |
| $PV_{LV}$ | PV delay for left ventricle |
| AV | Delay for a paced atrial event and a paced ventricular event |
| $AV_{optimal}$ | Optimal AV delay |
| $AV_{RV}$ | AV delay for right ventricle |
| $AV_{LV}$ | AV delay for left ventricle |
| Δ | Estimated interventricular delay (e.g., $AV_{LV}$-$AV_{RV}$) |
| $Δ_{programmed}$ | Programmed interventricular delay (e.g., a programmed VV delay) |
| $Δ_{optimal}$ | Optimal interventricular delay |
| IVCD_RL | Delay between an RV event and a consequent sensed LV event |
| IVCD_LR | Delay between an LV event and a consequent sensed RV event |
| $Δ_{IVCD}$ | Difference in interventricular conduction delays (IVCD_LR − IVCD_RL) |
| ΔP, ΔA | Width of an atrial event |
| PPD | Paced propagation delay (e.g., time from delivery of stimulation to an evoked response or feature of an evoked response) |

As described herein, a paced propagation delay (PPD) may be considered a "travel" time for a wavefront and may be measured from a delivery time of a stimulus to a feature time as sensed on a wavefront resulting from the stimulus (e.g., a feature of an evoked response). For examples, a paced propagation delay may be measured from a delivery time of a right ventricular stimulus to a maximum positive slope (e.g., repolarization) of an evoked response in the right ventricle.

Figure 6:
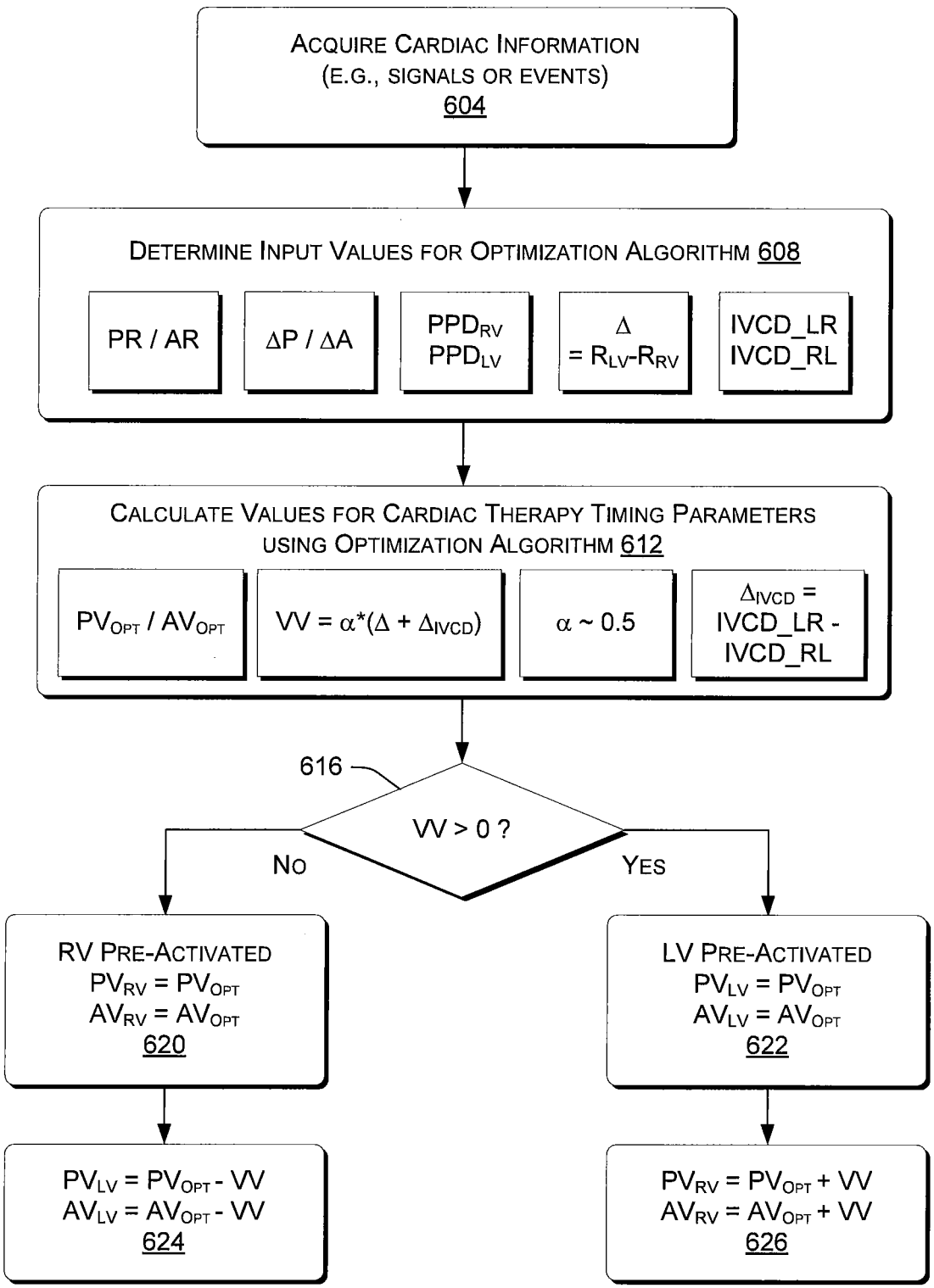
FIG. 6 is a block diagram of an exemplary method for optimizing one or more pacing parameters for ventricle pacing therapies.

FIG. 6 shows a block diagram of an exemplary method 600, which may be viewed as a more elaborate form of the method 450 of FIG. 4. The method 600 commences in an acquisition block 604 that acquires cardiac information. Cardiac information may be in the form of signals, events or a combination of signals and events. For example, a detection algorithm may detect an atrial event and a ventricular event and note a time for each of these events. With respect to signals, the acquisition block 604 may acquire electrograms that can be analyzed after their acquisition for any of a variety of features (e.g., a maximum slope as indicative of an evoked response, etc.).

In the example of FIG. 6, the method 600 includes a determination block 608 that determines input values for an optimization algorithm that can optimize timing parameters for delivery of cardiac therapy such as CRT. The input values shown in FIG. 6 include PR/AR, $\Delta P/\Delta A$, $PPD_{RV}/PPD_{LV}$, $\Delta$, IVCD_LR and IVCD_RL.

According to the method 600, a calculation block 612 calculates values for cardiac therapy timing parameters using the optimization algorithm. While the example of FIG. 6 refers to an optimization algorithm, programmer or device based software, or a look-up table may be used to determine the values of block 612. As indicated, the calculation block 612 calculates an optimum value for the parameter PV or AV (e.g., $PV_{Opt}$ or $AV_{Opt}$) and, for bi-ventricular pacing, it calculates an optimum value for VV. For example, W may be calculated using the following equation: $VV=\alpha^*(\Delta+\Delta_{IVCD})$ where $\alpha$ is a parameter assigned a value based on experience, patient performance data, etc. In practice, a value for $\alpha$ of about 0.5 has been used with good results.

Upon calculation of a value for the parameter VV, the method 600 enters a decision block 616 that decides if VV exceeds zero. The decision made by the decision block 616 dictates whether ventricular pacing should occur in first in the right ventricle or first in the left ventricle. In FIG. 6, if VV does not exceed zero then the right ventricle is paced first, as indicated in a block 620 "RV Pre-Activated" or "RV Master and LV Slave". However, if VV does exceed zero then the left ventricle is paced first, as indicated in a block 622 "LV Pre-Activated" or "LV Master and RV Slave". In either instance, a block follows 624 or 626, respectively, that calculates the PV or AV timing of the other ventricle based on VV. The various signs used in the method 600 rely on convention and may differ where the equations for $\Delta$ and $\Delta_{IVCD}$ differ.

Referring again to the parameter $\alpha$, a comparison between $\Delta$ and $\Delta_{programmed}$ or $\Delta_{optimal}$ can indicate a difference between a current cardiac therapy or state and a potentially better cardiac therapy or state. For example, consider the following equation:

$$\alpha=\Delta_{optimal}/\Delta$$

where $\alpha$ is an optimization parameter. Various echocardiogram and tissue Doppler image technique can be used to determine patient specific $\alpha$. However echocardiographic studies indicate that the parameter $\alpha$ is typically about 0.5. The use of such an optimization parameter is optional. The parameter $\alpha$ may be used as follows:

$$VV=\alpha^*(\Delta+\Delta_{IVCD})$$

If a parameter such as the aforementioned $\alpha$ parameter is available, then such a parameter is optionally used to further adjust and/or set one or more delays, as appropriate.

In many instances, cardiac condition will affect $AR_{RV}$ and $AR_{LV}$, and IVCD (e.g., IVCD_RL and/or IVCD_LR), which, in turn, may affect an existing optimal VV delay setting. As explained with respect to the method 450 of FIG. 4, various exemplary methods, devices, systems, etc., include calling for or triggering an algorithm to update an existing optimal VV delay according to a predetermined time or event period or activity sensors for exercise, resting, etc.

Figure 7:
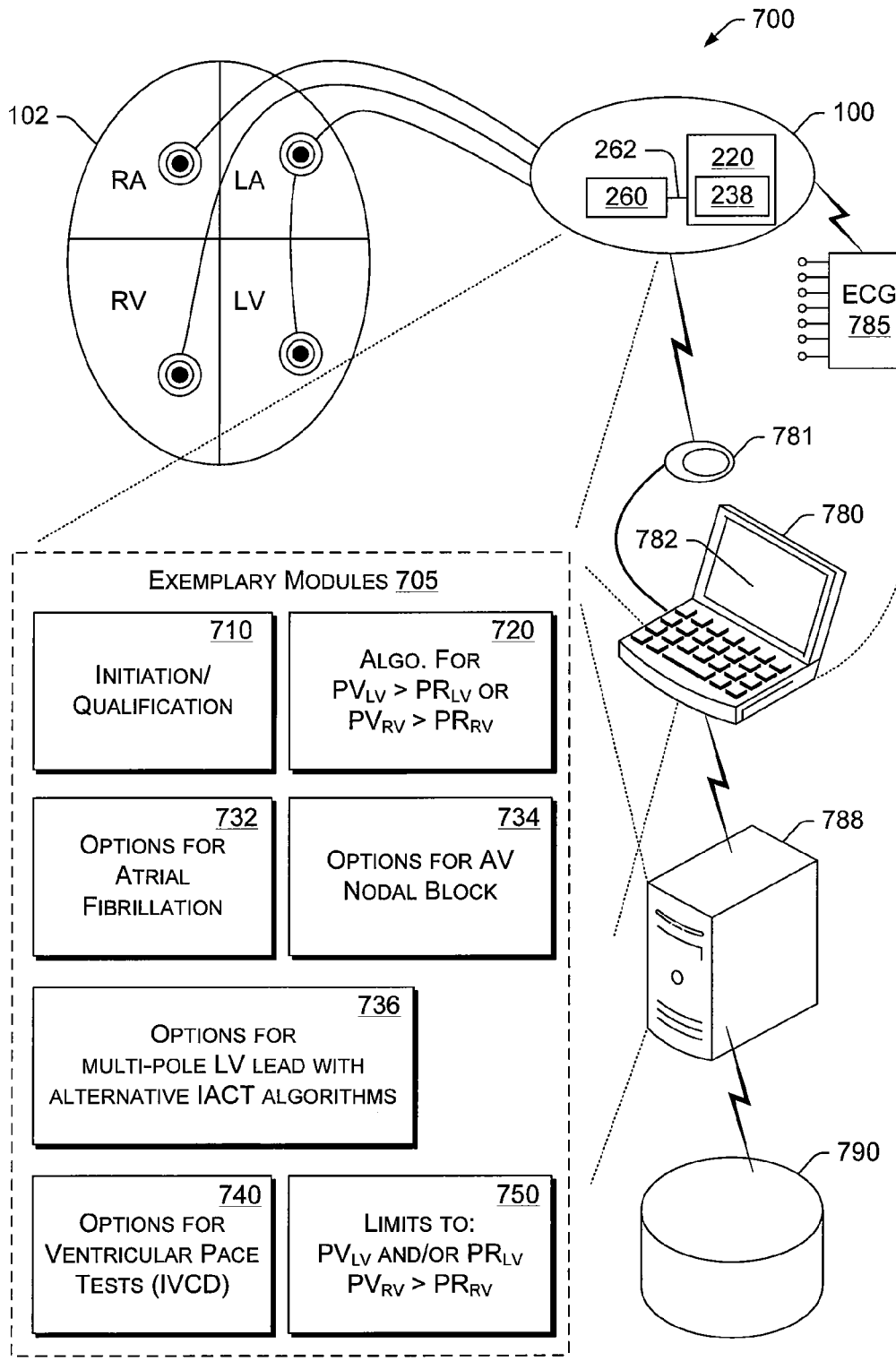
FIG. 7 is a diagram of an exemplary system capable of implementing various exemplary methods.

As described herein, various techniques can be used to optimize CRT. Such techniques may optionally include use of external measurement or sensing equipment (e.g., echocardiogram, etc.). Further, use of internal measurement or sensing equipment for sensing pressure or other indicators of hemodynamic performance is optional. Adjustment and learning may rely on IEGM information and/or cardiac other rhythm information. In general, the qualification method 410 of FIG. 4 aims to ensure that proper algorithms and/or techniques are selected for CRT optimization in patients that qualify for CRT FIG. 7 shows an exemplary system 700 that includes the exemplary implantable device 100 of FIGS. 1 and 2, with processor 220 including one or more modules 705, for example, that may be loaded via memory 260. A series of leads 104, 106 and 108 provide for delivery of stimulation energy and/or sensing of cardiac activity, etc., associated with the heart 102. Stylized bullets indicate approximate positions or functionality associated with each of the leads 104, 106 and 108. Other arrangements are possible as well as use of other types of sensors, electrodes, etc.

Memory 260 is shown as optionally including one or more of the modules 705. The modules 705 pertain to specific methods and/or algorithmic options for CRT and are described further below. In some circumstances, part of a method may be performed using a device other than the implantable device 100. For example, for acquisition of ECG information, an ECG unit 785 may be used, which optionally communicates with the device 100 or one or more other devices (e.g., the device 780, 788, etc.).

The system 700 may include other modules not shown in FIG. 7 for purposes such as programming the implantable device 100, performing measurements, determinations or calculations, displaying information, etc. For example, a module may cause a programmer device 780 to display control graphics on a display 782 whereby a clinician can actuate instructions via an associated displayed graphic to cause the implantable device 100 to measure PR or AR, to communicate PR or AR values to the device 780 and to display the PR or AR values on the display 782 of the device 780 (e.g., consider a button control labeled "Measure PR/AR").

In the example of FIG. 7, the system 700 includes the device programmer 780 having a wand unit 781 for communicating with the implantable device 100. The programmer 780 may further include communication circuitry for communication with another computing device 788, which may be a server. The computing device 788 may be configured to access one or more data stores 790, for example, such as a database of information germane to a patient, an implantable device, therapies, etc.

The programmer 780 and/or the computing device 788 may include modules that complement or interact with the modules 705, noting that a particular implementation of a method may use more than one device.

The programmer 780 optionally includes features of the commercially available 3510 programmer and/or the MERLIN™ programmer marketed by St. Jude Medical, Sylmar, Calif. The MERLIN™ programmer includes a processor, ECC (error-correction code) memory, a touch screen, an internal printer, I/O interfaces such as a USB that allows a device to connect to the internal printer and attachment of external peripherals such as flash drives, Ethernet, modem and WiFi network interfaces connected through a PCMCIA/CardBus interface, and interfaces to ECG and RF (radio frequency) telemetry equipment. The programmer 780 includes the display 782 for displaying one or more graphical user interfaces (GUIs), for example, to enable the method 410 of FIG. 4.

The wand unit 781 optionally includes features of commercially available wands. As shown, the wand unit 781 attaches to the programmer 780, which enables clinicians to conduct implantation testing and performance threshold testing, as well as programming and interrogation of pacemakers, implantable cardioverter defibrillators (ICDs), emerging indications devices, etc.

During implant, a system such as a pacing system analyzer (PSA) may be used to acquire information, for example, via one or more leads. A commercially available device marketed as WANDA™ (St. Jude Medical, Sylmar, Calif.) may be used in conjunction with a programmer such as the MERLIN™ programmer or other computing device (e.g., a device that includes a processor to operate according to firmware, software, etc.). Various exemplary techniques described herein may be implemented during implantation and/or after implantation of a device for delivery of electrical stimulation (e.g., leads and/or pulse generator) and the types of equipment for acquiring and/or analyzing information may be selected accordingly.

The wand unit 781 and the programmer 780 allow for display of atrial and ventricular electrograms simultaneously during a testing procedure. Relevant test measurements, along with customizable implant data, can be displayed, stored, and/or printed in a comprehensive summary report for the patient's medical records and physician review and/or for other purposes.

In the example of FIG. 7, the data store 790 may include information such as measures, values, scores, etc. Such information may be used by a model, in making a comparison, in making a decision, in adjusting a therapy, etc. Such information may be updated periodically, for example, as the device 100 (or other device(s)) acquires new patient information. The system 700 is an example as other equipment, instructions, etc., may be used or substituted for features shown in FIG. 7.

Referring to the modules 705 of FIG. 7, the module 710 pertains to initiation and/or qualification of CRT for a patient. The module 710 may instruct or call for use of one or more other modules such as the modules 720, 732, 734, 736, 740 and 750. The module 710 can enforce initial testing by the programmer 780 prior to turning on a CRT algorithm and/or CRT optimization algorithm of the device 100. The module 710 can also call for use of one or more algorithms to handle special cases (e.g., based on cardiac condition). Where certain measurements prove problematic or unreliable for purposes of accurate CRT optimization, the module 710 can call for algorithms or techniques that address such issues. The module 710 can also optionally call for setting of safety limits, for example, to eliminate inappropriate PV/AV and VV delays.

The module 720 includes algorithms that address a particular class of cardiac condition. Specifically, the module 720 can implement one or more special algorithms for patients that exhibit the condition $PV_{LV} > PR_{LV}$ ($AV_{LV} > AR_{LV}$) or the condition $PV_{RV} > PR_{RV}$ ($AV_{RV} > AR_{RV}$).

The module 732 includes one or more algorithms that address atrial fibrillation, the module 734 includes one or more algorithms that address atrio-ventricular nodal block, and the module 736 includes one or more algorithms for a multi-pole left ventricular lead or alternative IACT algorithms. For example if a multi-pole left ventricular lead is available (e.g., a quadpole lead), a user interface provides options for selecting algorithms for IACT. By using the algorithms for the LV lead, LA activation signals can be sensed from the selected pole of a LV lead and IACT can be calculated. The LA signals from the LV lead can be located by timing RA signals and the QRS from RV lead or the tip electrode of LV lead.

The module 740 includes one or more algorithms that address ventricular pacing tests for measurement of IVCDs and the module 750 pertains to limits for one or more CRT parameters.

Figure 8:
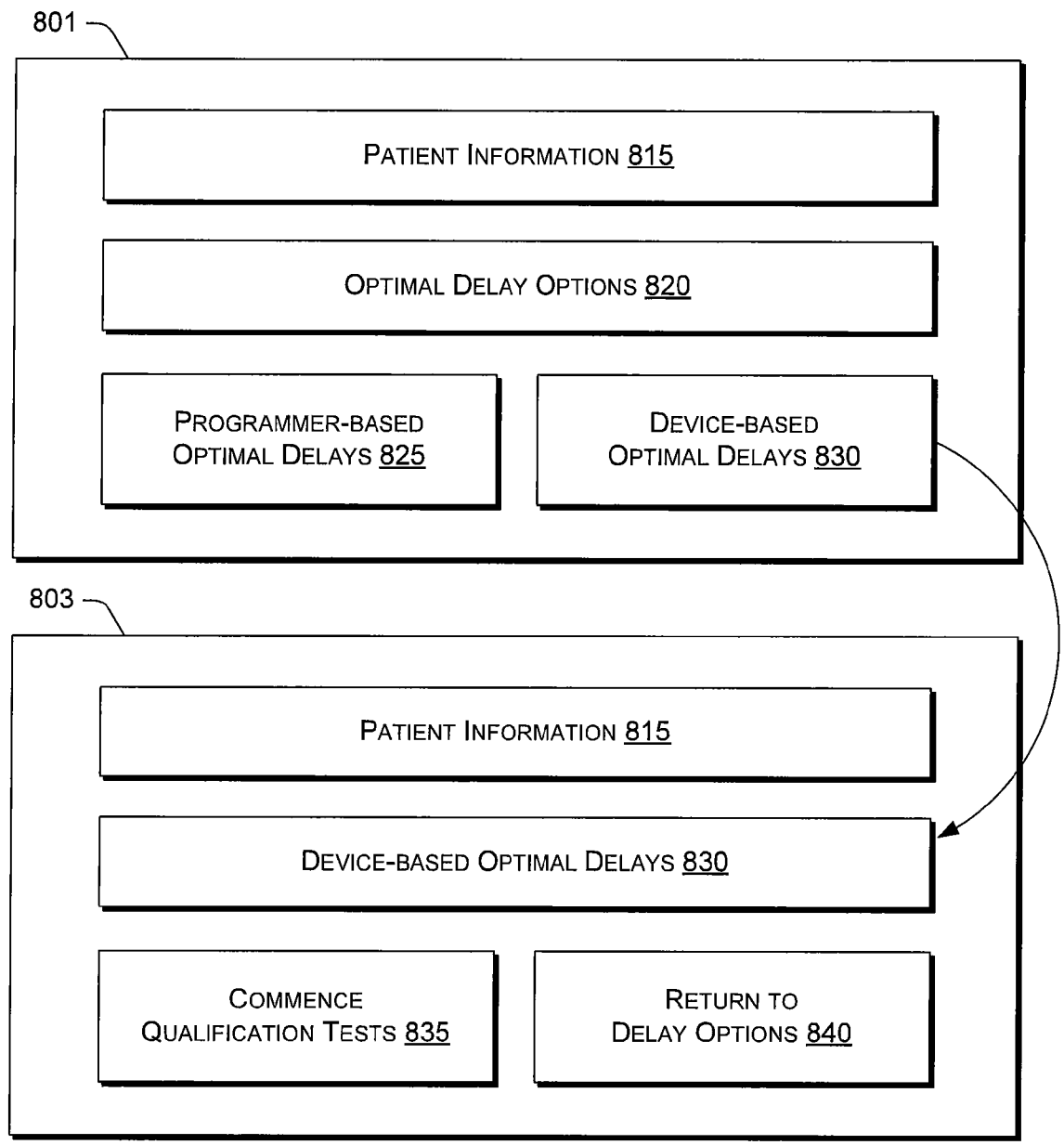
FIG. 8 is a diagram of exemplary GUIs for guiding a clinician.

FIG. 8 shows two graphical user interfaces (GUIs) 801 and 803 that may be displayed by the device 780 of FIG. 7 (e.g., optionally sequentially on the display 782). The GUI 801 includes a field for patient information 815, a field for optimal delay options 820, a field for programmer-based optimal delays 825 and a field for device-based optimal delays 830 (e.g., per the method 450 of FIG. 4). The GUI 801 allows for selection of options presented in one or more of the fields. For example, when a device-based optimal delay is selected per the field 830, the GUI 803 is displayed (e.g., to the same display). The GUI 803 guides a clinician along a path for deciding whether a device can implement one or more CRT optimization algorithms.

In the example of FIG. 8, the GUI 803 displays a field 830 to indicate the selected option along with a field 835 to commence qualifications tests and a field 840 to return to a previous GUI. For example, the programmer display 782 of the programmer 780 may display "Optimal Delays", which leads to options of "Programmer-based QuickOpt™" and "Device-based QuickOpt™". Upon selection of the "Device-based QuickOpt™" option, the programmer 780 displays an option to commence initial testing before allowing the clinician to access an "ON" button for turning on device-based QuickOpt™ algorithms.

Figure 9:
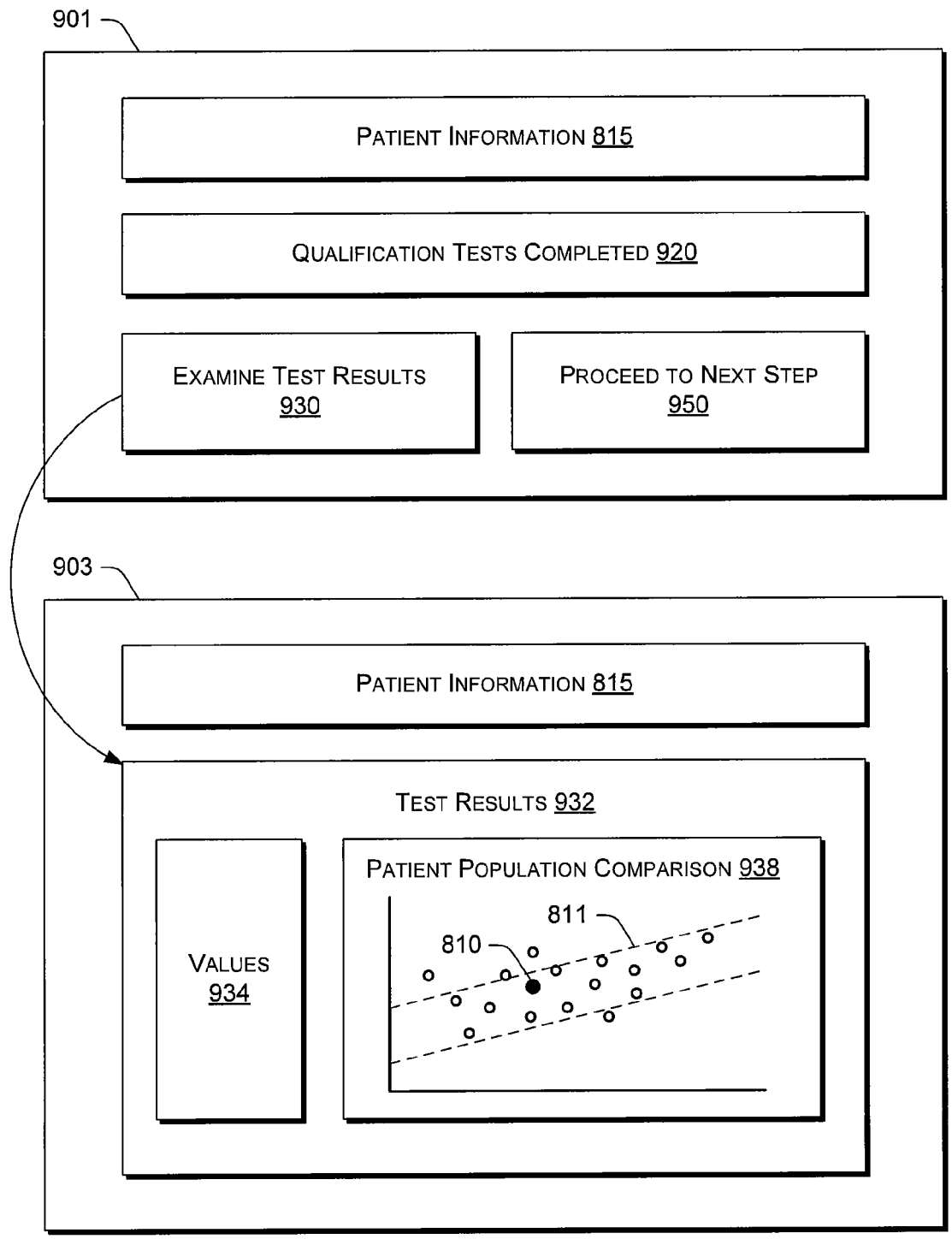
FIG. 9 is a diagram of exemplary GUIs for guiding a clinician where one GUI includes a comparison of information for a specific patient to information for a patient population.

FIG. 9 shows exemplary GUIs 901 and 903 as presenting information and options related to qualification tests. The GUI 901 includes a field for patient information 815, a field for notification that tests have been completed 920, a field to examine test results 930 and a field to proceed to a subsequent step 950.

The field 930 allows a user to examine test results, for example, as presented in the GUI 903. The GUI 903 includes a field for patient information 815 and a test results field 932. In the example of FIG. 9, the test results field 932 includes a values field 934 for displaying numeric values and a data analysis field 938 for displaying information graphically. For example, a data point 810 for a patient may be displayed with respect to data for a patient population along with qualification information 811. The qualification information 811 may act as criteria for helping a clinician decide whether a particular algorithm should be implemented or not. The qualification information 811 may be used to automatically determine whether a particular algorithm should be implemented or not. For example, the qualification information 811 may be used in the decision block 426 and/or the decision block 430 of the method 410 of FIG. 4.

Figure 10:
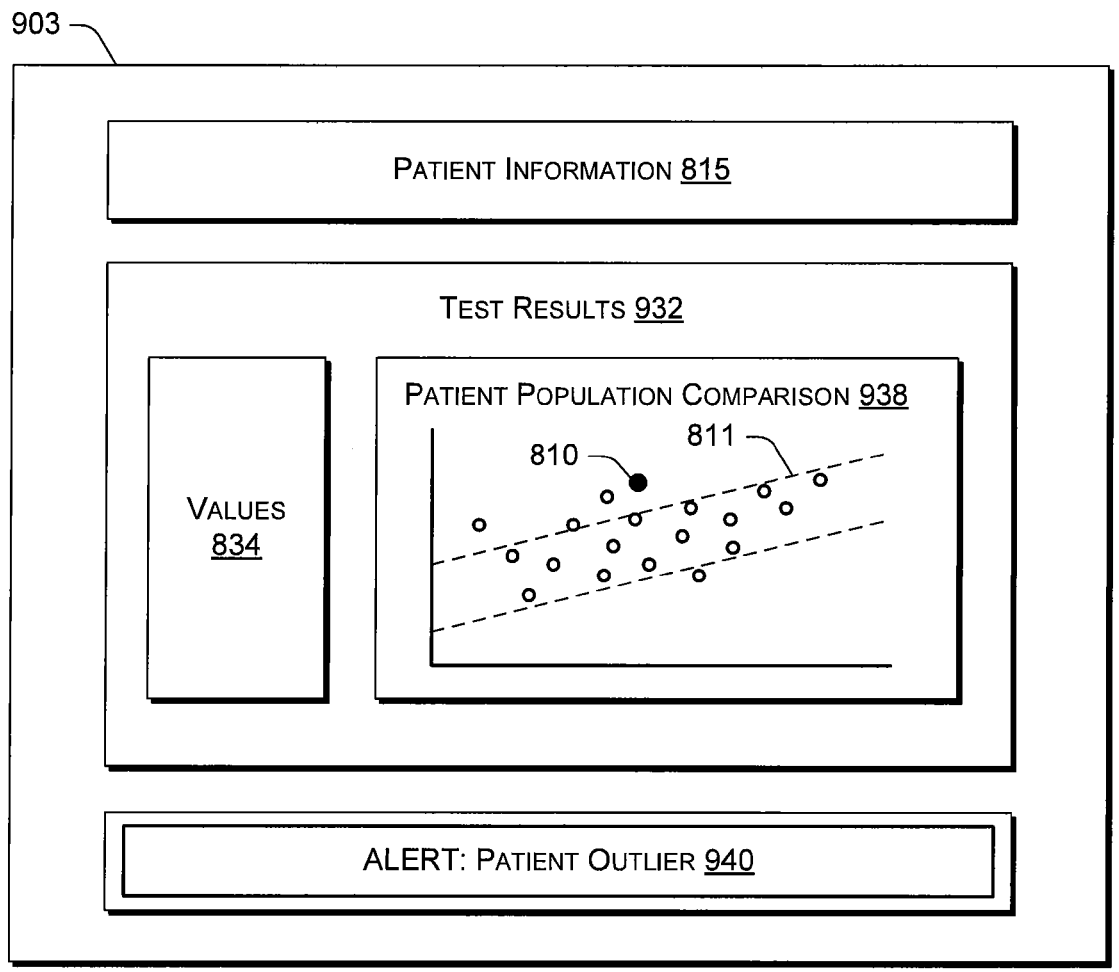
FIG. 10 is a diagram of exemplary GUIs for guiding a clinician when a patient exhibits a particular cardiac condition.
Figure 10:
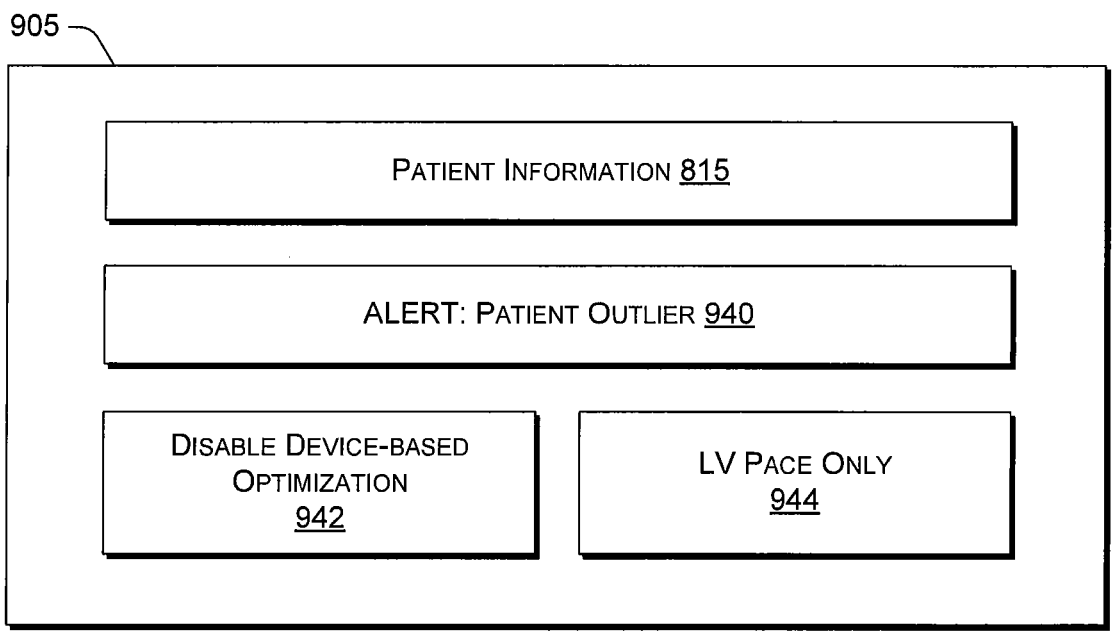

Such features allow clinicians to examine test results and decide if a particular algorithm(s) is appropriate for the patient or whether the patient is an "outlier" (e.g., outside the bounds determined by the qualification information 811). For example, FIG. 10 shows a GUI 903 and a GUI 905 for a different patient. In the example of FIG. 10, the patient data 810 is outside the bounds 811 and therefore the patient is an outlier. In response, the programmer displays an alert field 940 that alerts a user that the patient does not compare favorably to a particular patient population.

In response, a user may select to proceed where the programmer displays the GUI 905. The GUI 905 includes a field 942 for disabling device-based optimization and a field 944 for LV pacing only. The field 944 may be displayed automatically based on an analysis of patient information.

As described herein, a programmer or other computing device may display any of a variety of options for CRT such as those mentioned with respect to the module 705 of FIG. 7. Examples include "LV pace only" for LV first or "RV pace only" for RV first, "Negative Hysteresis ON", etc. (see, e.g., options of the method 300 of FIG. 3). In some cases, other means such as echo/TDI can be suggested on the display for purposes of assessing patient condition and/or optimization. As mentioned, other cases include patients with heart block or in AF, or "LV pace" test competing with intrinsic conduction to RV leads.

Figure 11:
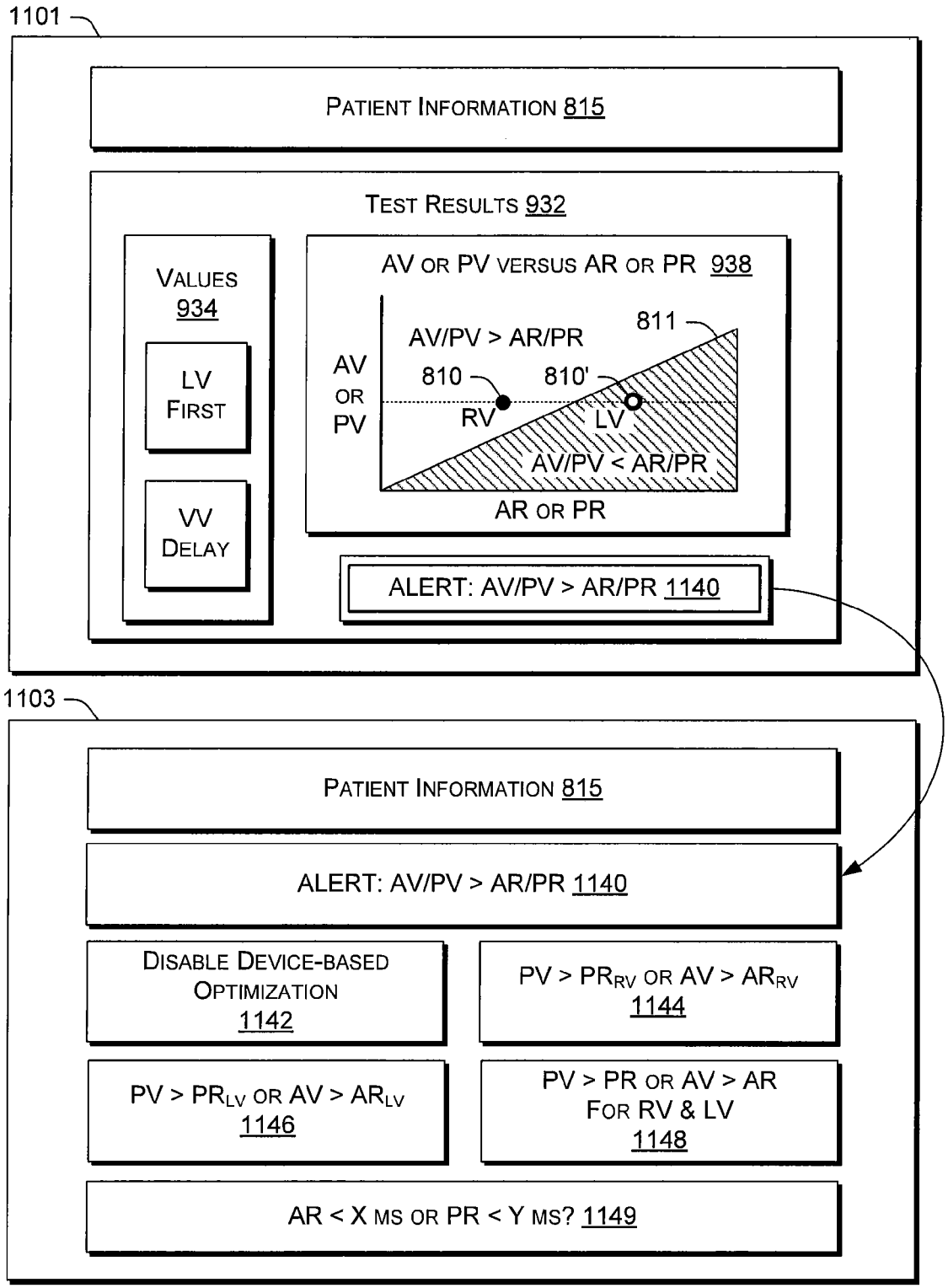
FIG. 11 is a diagram of exemplary GUIs for guiding a clinician when a patient exhibits a particular cardiac conduction condition.

FIG. 11 shows two GUIs 1101 and 1103 as related to the module 720 of FIG. 7. The GUI 1101 includes the values field 934 that indicates LV first pacing (i.e., the left ventricle should be paced prior to the right ventricle for optimal CRT) and a VV delay value. A data plot field 938 includes patient data for the RV 810 and patient data for the LV 810'. Qualification information 811 is represented as a line that divides the plot into a portion where AV/PV>AR/PR and a portion where AV/PV<AR/PR.

As described herein, algorithms exist to handle PV (or AV)>PR (or AR). For the QuickOpt™ CRT algorithms, tests are included of either $PR_{RV}$ and $PR_{LV}$ or $AR_{RV}$ and $AR_{LV}$ with "V sense" and for RR delays at RV and LV leads. At the completion of all the standard QuickOpt™ tests, VV delays are suggested with either SIM, or LV first or RV first. If LV first and PV or AV<$PR_{LV}$ or $AR_{LV}$, the programmer can suggest a LV sensing configuration even though PV>$PR_{RV}$ or AV>$AR_{RV}$ (see, e.g., the plot field 938).

If PV or AV are greater than both $PR_{RV}$ and $PR_{LV}$ (or both $AR_{RV}$ and $AR_{LV}$), more comparisons can be performed. If PR or AR is too short (such as less than about 80 ms), other means of optimization can be suggested and displayed.

The GUI 1103 includes the alert field 1140 along with fields for disabling device-based optimization 1142 and various aforementioned conduction conditions 1144, 1146 and 1148. A field 1149 allows a clinician to select options where AR<X ms or PR<Y ms. In the field 1149, the values for X and Y may differ or be the same. Information may appear in the field 938 to indicate when such conditions occur.

Figure 12:
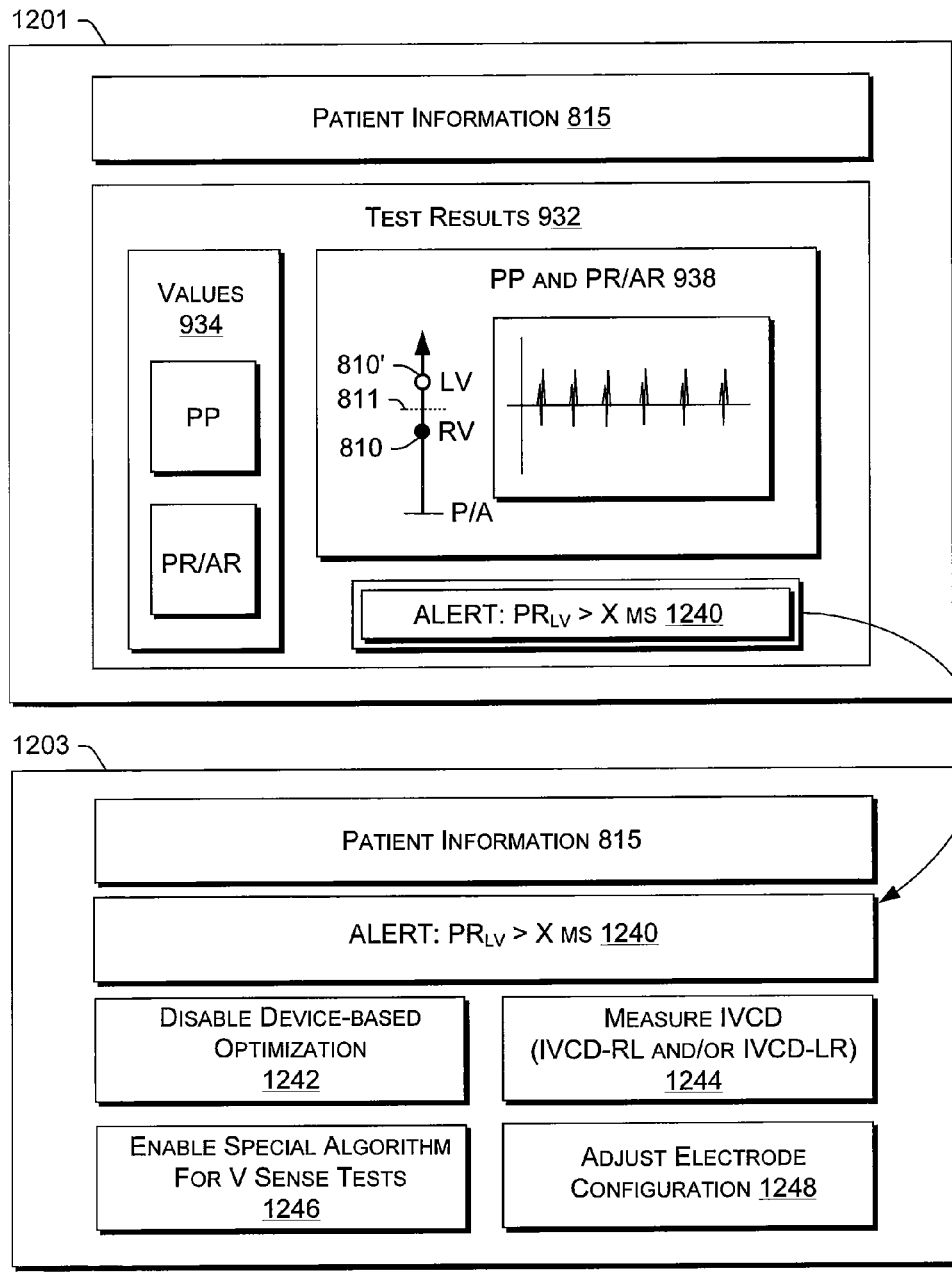
FIG. 12 is a diagram of exemplary GUIs for guiding a clinician when a patient exhibits a particular cardiac conduction condition.

FIG. 12 shows two GUIs 1201 and 1203 that pertain to a patient with a $PR_{LV}$ or an $AR_{LV}$ that exceeds a threshold. The GUI 1201 includes a test results field 932 that includes a values field 934 that displays a PP interval value and a PR/AR value. The GUI 1201 also includes a field 938 for displaying patient data such as PP interval (e.g., atrial IEGM) and patient PR or AR data for the right ventricle 810 and the left ventricle 810' along with a threshold value 811. An alert field 1240 indicates that $PR_{LV}$>X ms for the patient.

The GUI 1203 includes the field 1240 to indicate that this condition exists along with a field 1242 to disable device-based optimization, a field 1244 to measure IVCD(s), a field 1246 to enable a special algorithm for V sense tests and a field 1248 to adjust electrode configuration for an implantable device.

As described with respect to FIG. 7, various techniques can address patients with conditions such as AF, AV nodal block, LBBB and/or RBBB. For example, if PR or AR is too long (e.g., greater than about 325 ms) or if patients are in AF, a special algorithm can replace standard "V sense" tests. The GUI 1203 displays this option in the field 1246, which may be selected by a clinician.

Figure 13:
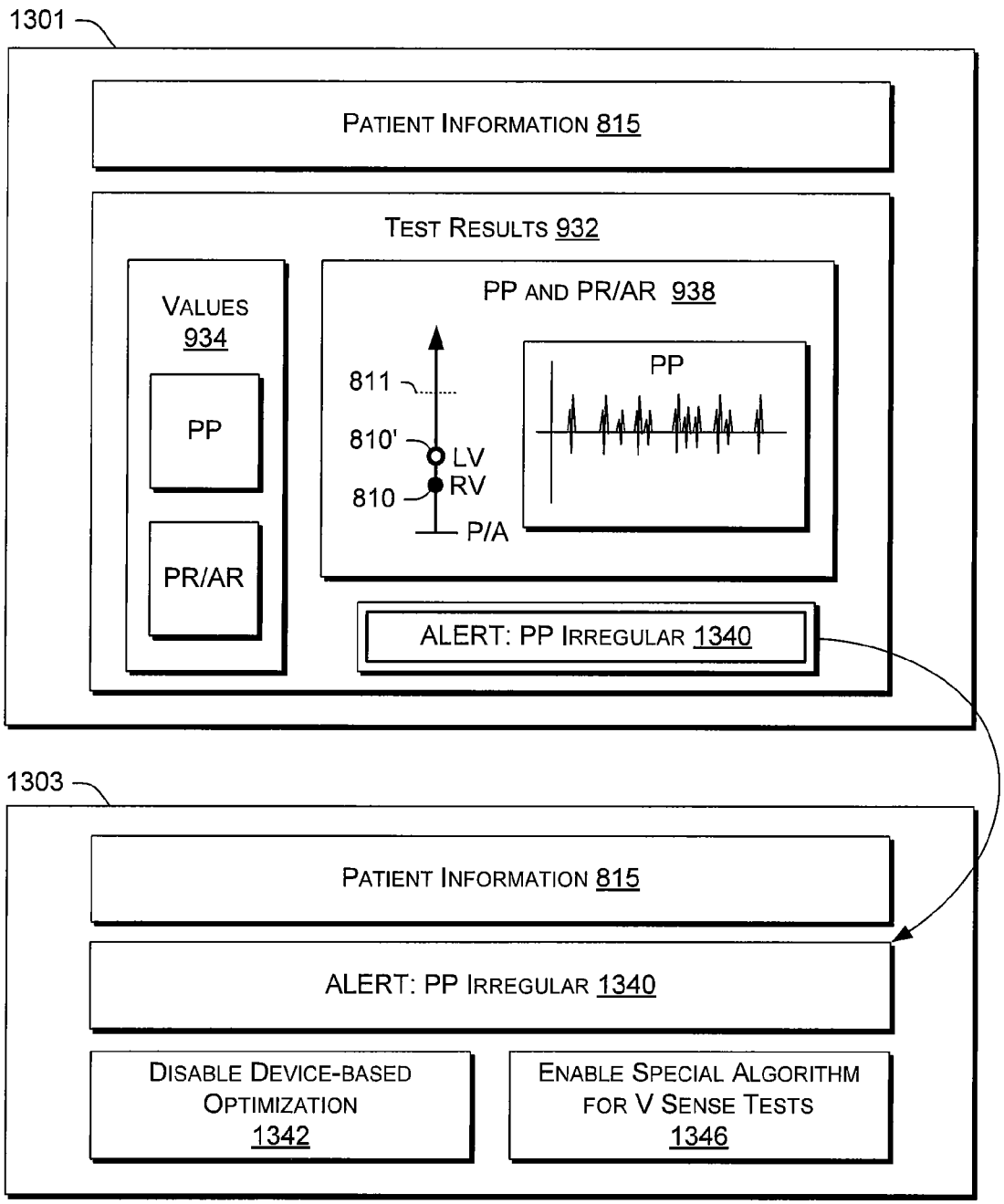
FIG. 13 is a diagram of exemplary GUIs for guiding a clinician when a patient exhibits an atrial arrhythmia.

FIG. 13 shows exemplary GUIs 1301 and 1303 as pertaining to a patient with an atrial arrhythmia (e.g., AF, AT, etc.). A data field 938 includes a plot of atrial information (e.g., atrial IEGM) and an alert field 1340 indicates that the PP interval is irregular for the patient. The GUI 1303 displays a field 1342 to disable device-based optimization and a field 1346 to enable a special algorithm for use with patients that experience irregular atrial activity.

For patients in AF, QuickOpt™ tests may become unreliable for both "LV pace" and "RV pace" tests. Further, during episodes of AF, pacing modes VVI or DDI will be commonly used and AV synchrony is no longer accessible. Pacing asynchronously would result in various situations for fusion beats or sensed conducted beats from atria due to irregular atrioventricular conduction. As indicated in the GUI 1303, fields 1342 and 1346 are displayed for options: a) replacement of "V sense" tests by "RV pace" tests and selecting V pacing rate in VVI or DDI mode; and b) do not enable QuickOpt™ for VV optimization. In the latter case, other means may be used to determine optimal VV delay.

Figure 14:
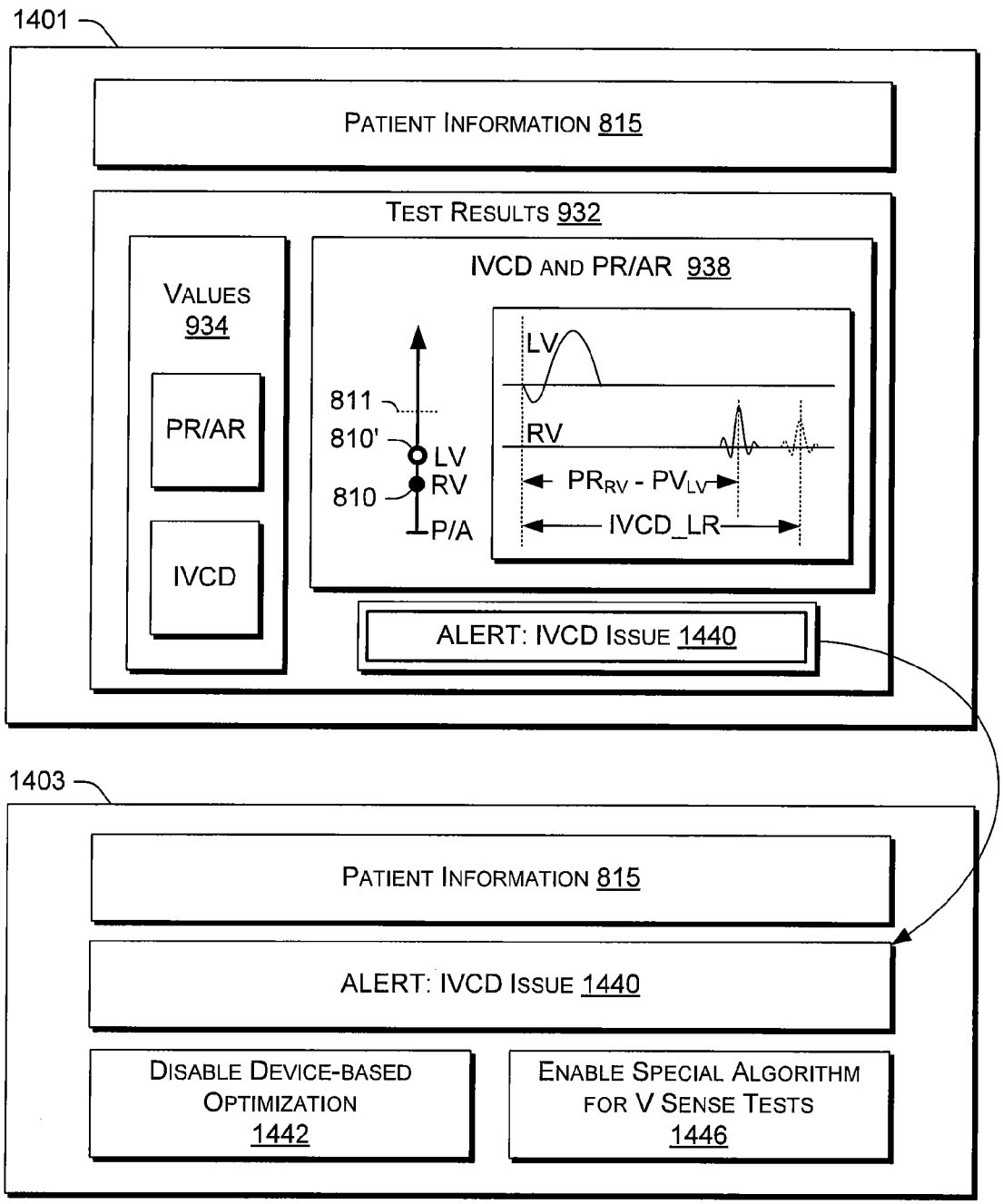
FIG. 14 is a diagram of exemplary GUIs for guiding a clinician when a patient exhibits a condition that can confound measurement of an interventricular conduction delay.

FIG. 14 shows exemplary GUIs 1401 and 1403 pertaining to cardiac conditions where measurement of IVCD may be problematic or inaccurate for IVCD_RL or IVCD_LR. The GUI 1401 includes a values field 934 that displays PR/AR values and IVCD values, as appropriate. A data field 938 displays a plot of LV and RV IEGM data while an alert field 1340 indicates that an issue exists for measurement of IVCD_LR. Specifically, as the interval $PR_{RV}$–$PV_{LV}$ is less than IVCD_LR, measurement of IVCD_LR may be unreliable.

QuickOpt™ tests for IVCD_LR are referred to as "LV Pace" where a pacing stimulus is delivered to the left ventricle and a corresponding response sensed in the right ventricle. Data indicate that difficulties occur with "LV pace" tests when patients have long inter-ventricular delays (IVCD). In these cases, intrinsic beats from the atria reached the RV sensing electrode(s) prior to paced LV propagation. For example, if IVCD_LR takes 120 ms with a PV of 80 ms, the time delay from the sensed P wave to paced LV reaching RV lead is 200 ms. In these cases when PR interval for a patient is less than about 200 ms, the RV lead will sense the intrinsic beats resulting errors in "LV pace" tests of QuickOpt™ algorithm.

The GUI 1403 includes a field 1442 for disabling device-based optimization and a field 1446 for enabling a special algorithm for V sense tests. Such information may be presented in response to a user selecting the alert field 1440 in the GUI 1401. As actual data can be displayed in the field 938, a clinician can verify that the issue exists and determine a course of action as guided by the programmer or by other knowledge.

As described herein, for the QuickOpt™ algorithms, a test is performed to determine if $PR_{RV}$<IVCD_LR+PV short (e.g., "PV short" having a default value of about 50 ms) for "V sense" tests where $\Delta = R_{LV} - R_{RV}$>0. In another approach, an exemplary method selects Min($PR_{LV}$, $PR_{RV}$) and uses the lead with the longer PR and measures IVCD. Such a method can enable this feature if the shorter PR is less than the sum of IVCD and PV, where PV may be about 50 ms.

An exemplary method can automatically perform one or more tests according to algorithm related criteria and report the test results. Depending on the results and the criteria, such a method can display options for selection by a clinician. For example, options may include: a) selection of different PV or AV delays for "LV pace" tests such as "50/25 ms", "70/50 ms", "100/70 ms" and rerun one or more tests; b) replacement of "RV pace" and "LV pace" tests with pacing latency at RV and LV leads or, more generally, paced propagation delay (PPD); c) changing the V pace rate and mode in VVI; and d) not enabling one or more algorithms and indicating that other means may be used for optimizing one or more CRT parameters.

With respect to PPD, an exemplary technique can determine a surrogate for the parameter Δ, based in part on PPD. For example, consider an RV lead positioned at the endocardial apex where use of this lead in conjunction with an LV sensing lead can provide a surrogate value for the parameter Δ according to the equation IVCD_RL–PPD$_{RV}$. Similarly, such a technique may be used for the left ventricle (IVCD_LR–PPD$_{LV}$). In some instances, a RV Δ$_{Sur}$ and a LV Δ$_{Sur}$ may be determined and one or both (e.g., an average) may be used in place of a "V sense" based A value. In practice, the RV variation may be preferred, especially for patients with conditions such as left bundle branch block (LBBB), which is a found in some HF patients.

Figure 15:
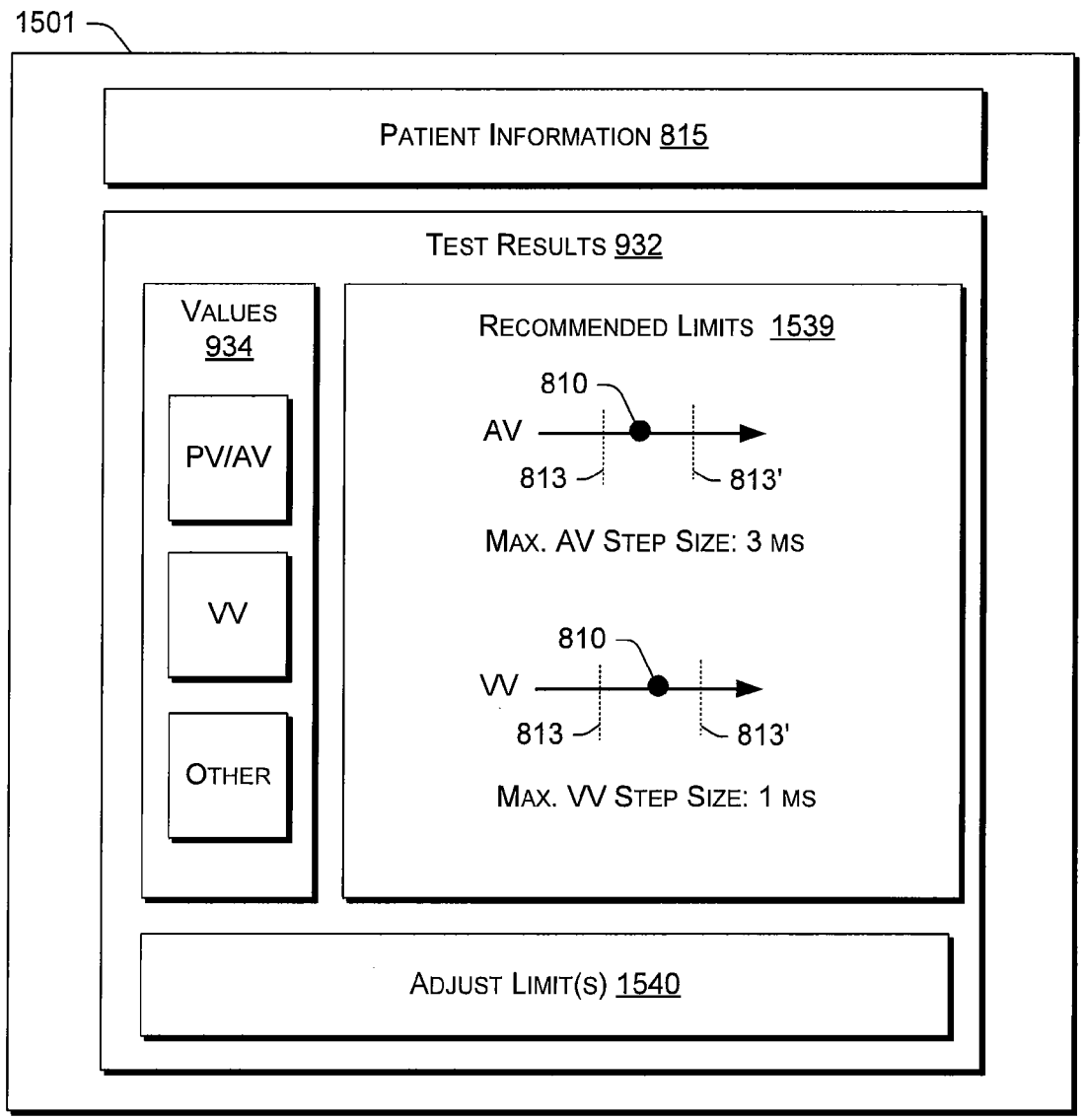
FIG. 15 is a diagram of an exemplary GUI for guiding a clinician as to limits associated with CRT optimization.

FIG. 15 shows an exemplary GUI 1501 for displaying limits for limiting adjustments to one or more CRT parameters. The GUI 1501 includes a values field 934 that displays values such as PV/AV, VV and/or other values. The GUI 1501 also includes a field 1539 for displaying recommended limits on AV step size and VV step size. In the example of FIG. 15, the AV step size is limited to about 3 ms while the VV step size is limited to about 1 ms. The field 1539 also shows current AV/VV values 810 for a patient with respect to lower limits 813 and upper limits 813'.

A limits feature for delays may be enabled by a clinician and act to ensure some degree of safety for delivery of CRT. While this feature is turned on, automatically updating delays can be controlled by criteria built in a module of an implantable device while limits of changes in delays can be programmable, for example, using the GUI 1501 (e.g., by selecting a field 1540 for adjusting one or more limits).

In a particular example, a call to adjust a delay outside of a bound will result in no adjustment to the delay. Default limits for adjustments can be, for example, about 5 ms for a minimum change to W and about 10 ms as a minimum for PV or AV and about 20 ms for a maximum change to W and about 30 ms as a maximum to PV or AV (e.g., as compared with current delay settings). Adjustments less than a minimum value or greater than a maximum value can be programmed to result no updating and therefore act to avoid the risk of inappropriate PV/AV and VV delays.

In a particular example, a clinician can enter a maximum VV delay allowed with either LV first or RV first of about 40 ms and a maximum PV delay of about 200 ms (e.g., with a maximum AV delay of about 250 ms).

For an implantable CRT device with the QuickOpt™ algorithm enabled, if the algorithm were to fail to complete tests successfully or test results fail to meet set criteria, delay settings can remain unchanged and the QuickOpt™ can be scheduled at, for example, pre-set intervals (e.g., of about 20 minutes) for one or more additional attempts at optimization. If a second test fails, QuickOpt™ tests may be automatically postponed to a next scheduled time.

In addition, at the initiation of a device QuickOpt™ algorithm option, a clinician can review initial tests and decide if it is appropriate to turn this feature on. Appropriate initial test results can be stored in an implantable device and/or elsewhere, for example, to allow for baseline comparisons. An exemplary implantable device with optimization algorithms for CRT can store test results so that a clinician can review the results at an office visits (or remotely), which can assist in assessing patient health (e.g., improving cardiac condition, worsening cardiac condition, etc.).

In the system 700, a database may store results from various patient tests. With validation studies in echo AVTI and TDI, the chance of inappropriate delays from an optimization algorithm for one or more CRT parameters may be expected to be similar to that of echo/TDI techniques.

Various examples presented herein refer to special algorithms for addressing certain cardiac conditions. As described herein, various exemplary special algorithms provide for measurement of IVCD_RL or IVCD_LR where (i) interventricular conduction delay exceeds an atrio-ventricular delay and where (ii) abnormal atrial activity such as atrial fibrillation exists.

Figure 16:
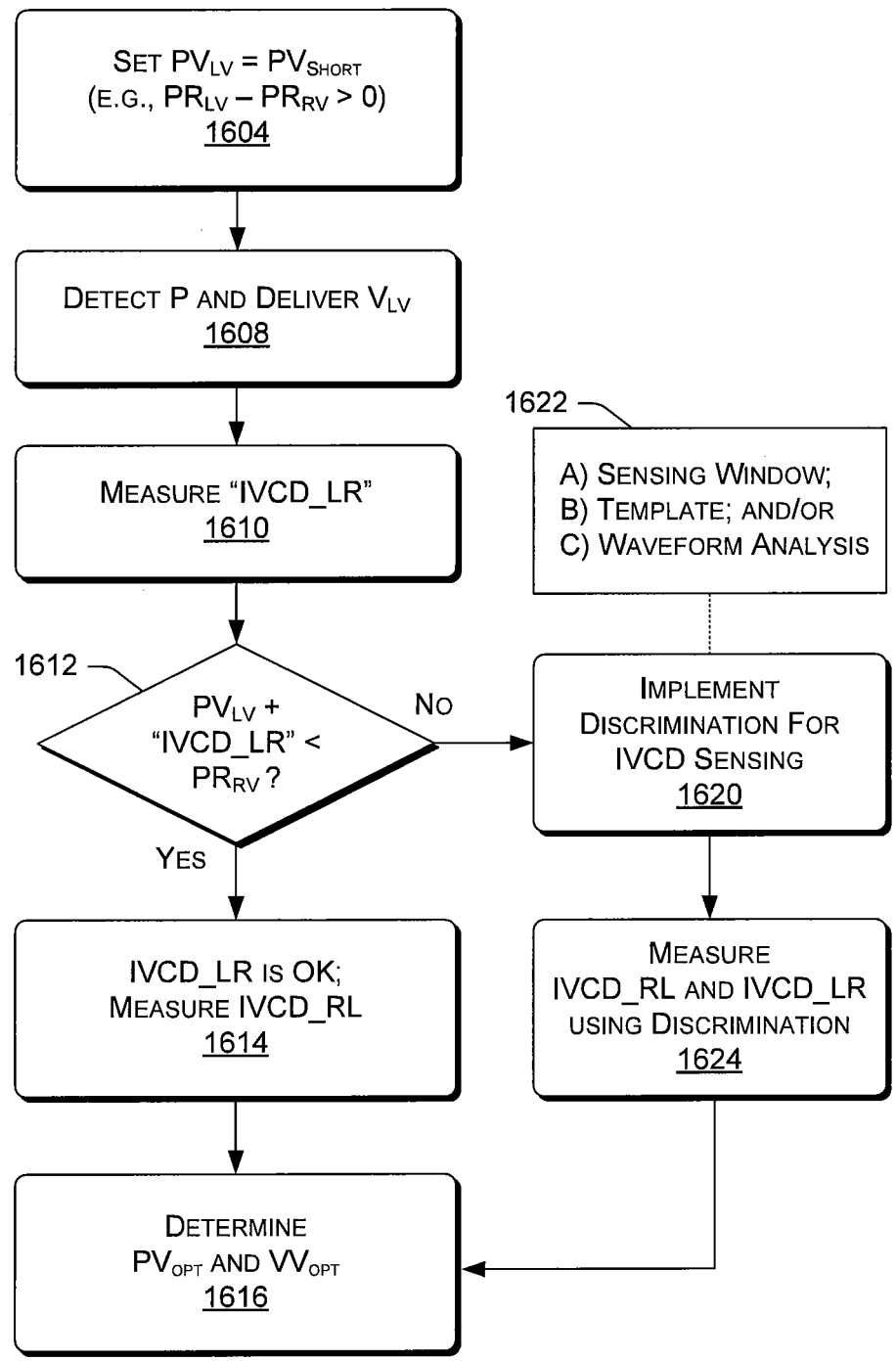
FIG. 16 is a diagram of an exemplary algorithm for measuring one or more interventricular conduction delays.

FIG. 16 shows a particular algorithm 1600 for cardiac conditions or other conditions that may confound IVCD measurements. Such a method may be used by a programmer when deciding whether to initiate CRT for a patient and/or device-based optimization of one or more CRT parameters. The method 1600 commences in a set block 1604 that sets PV$_{LV}$ to a short value, for example, per a parameter PV$_{Short}$ (e.g., about 50 ms). The set block 1604 may select the left ventricle or the right ventricle. For example, where PR$_{LV}$ exceeds PR$_{RV}$ (e.g., PR$_{LV}$–PR$_{RV}$>0) the set block 1604 selects the left ventricle and where PR$_{RV}$ exceeds PR$_{LV}$ (e.g., PR$_{LV}$–PR$_{RV}$<0) the set block 1604 selects the right ventricle (e.g., PV$_{RV}$=PV$_{Short}$).

The method 1600 continues in a detection and delivery block 1608 that detects an atrial event (P) and delivers a stimulus to the left ventricle (V$_{LV}$) according to PV$_{LV}$, which has been set to PV$_{Short}$. A measurement block 1610 follows that measures "IVCD_LR" by sensing activity in the right ventricle. The measured "IVCD_LR" may be accurate as caused by the left ventricular stimulus or it may be inaccurate as caused by a conducted atrial event. Per a decision block 1612, if the sum PV$_{LV}$+"IVCD_LR" is less than PR$_{RV}$, then it is likely "IVCD_LR" is an accurate measurement of the left ventricle to right ventricle interventricular conduction delay and the method 1600 continues at measurement block 1614, whereas, if the sum PV$_{LV}$+"IVCD_LR" is equal to or greater than PR$_{RV}$, then it is likely "IVCD_LR" is an inaccurate measure of the left ventricle to right ventricle interventricular conduction delay and the method 1600 continues at the implementation block 1620.

As indicated by the measurement block 1614, if PV$_{LV}$+"IVCD_LR" is less than PR$_{RV}$, then the measured IVCD_LR per block 1610 is deemed reliable (i.e., OK). Further, it is likely that IVCD_RL can be accurately measured if PV$_{RV}$ is set to PV$_{Short}$ as PR$_{LV}$ is greater than PR$_{RV}$. After the measurement block 1614, the method 1600 enters a determination block 1616 that determines PV$_{Opt}$ and VV$_{Opt}$, for example, according to an algorithm of the method 600 of FIG. 6.

Per the decision block 1612, if the method 1600 enters the implementation block 1620, a discrimination technique is used to measure at least IVCD_LR, per a measurement block 1624. The method 1600 then continues at the determination block 1616 to determine PV$_{Opt}$ and VV$_{Opt}$, for example, according to an algorithm of the method 600 of FIG. 6.

Some discrimination techniques are shown in block 1622, which include A) a sensing window; B) a template; and C) waveform analysis. A sensing window may commence sensing activity in the right ventricle after a time PR$_{RV}$, given that PR$_{RV}$ is less than PV$_{LV}$+"IVCD_LR", per block 1612. Further, PV$_{Short}$ (e.g., for PV$_{LV}$) may be increased by about 5 ms to about 10 ms, which would delay the conducted right ventricular event in the case that PR$_{RV}$ is about the same as PV$_{LV}$+IVCD_LR.

As mentioned, cardiac conditions such as atrial fibrillation may confound measurement of IVCD_LR or IVCD_RL. An exemplary method can enables an "AF" option that can optionally measure IVCD_LR and/or IVCD_RL in the presence of atrial fibrillation. Once the AF option is enabled, the method then monitors cardiac activity for presence of AF. For example, a decision block can decide if a patient is experiencing AF. The decision block may be part of an algorithm that aims to optimize one or more pacing parameters (e.g., $PV_{Opt}$, $AV_{Opt}$, $VV_{Opt}$) where optimization relies on measurement of IVCD_LR and/or IVCD_RL. If the decision block decides that a patient is experiencing AF, then the method continues at an implementation block that implements a discrimination technique for measurement of IVCD_LR and/or IVCD_RL. A measurement block then uses the discrimination technique to more accurately measure IVCD_LR and/or IVCD_RL in the presence of AF.

While the foregoing method includes use of a discrimination technique in the presence of AF, an exemplary method may take other action. For example, a method may implement a wait period and/or call for anti-atrial fibrillation therapy prior to measurement of IVCD_RL and/or IVCD_LR.

While atrial fibrillation is mentioned, various exemplary techniques may account for any of a variety of supraventricular tachycardia (SVTs). SVT, a common clinical condition, is any tachyarrhythmia that requires atrial and/or AVN tissue for its initiation and maintenance. It is usually a narrow-complex tachycardia that has a regular, rapid rhythm; however, exceptions include atrial fibrillation (AF) and multifocal atrial tachycardia (MFAT). Aberrant conduction during SVT results in a wide-complex tachycardia. SVTs can occur in persons of all age groups, and treatment can be challenging. Paroxysmal supraventricular tachycardia (PSVT) is episodic, with an abrupt onset and termination. Manifestations of SVT are quite variable and patients may be asymptomatic or they may present with minor palpitations or more severe symptoms.

CONCLUSION

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A method, implemented by a computing device, the method comprising:
    receiving patient information for a patient;
    analyzing the patient information; and
    based on the analyzing, deciding if the patient qualifies for automatic, implantable device-based optimization of one or more cardiac resynchronization therapy; and,
    for a patient qualified for automatic, implantable device-based optimization of one or more cardiac resynchronization therapy parameters, presenting a graphical user interface that comprises a selectable control to enable an algorithm of an implantable device to automatically optimize at least one of the one or more cardiac resynchronization therapy parameters;
    otherwise, presenting a graphical user interface that comprises a notice that the patient does not qualify and that does not comprise a selectable control to enable an algorithm of an implantable device to automatically optimize the one or more cardiac resynchronization therapy parameters.

2. The method of claim 1 wherein the receiving comprises instructing an implantable device to perform one or more tests.

3. The method of claim 1 wherein the analyzing comprises comparing the patient information to requirements of the algorithm.

4. The method of claim 1 wherein the algorithm requires a test that delivers energy to one ventricle and senses cardiac activity responsive to the delivered energy in the other ventricle.

5. The method of claim 4 wherein the deciding decides not to qualify the patient for optimization if the test cannot reliably sense cardiac activity in response to the delivered energy in the other ventricle due to a prolonged interventricular conduction condition.

6. The method of claim 4 wherein the deciding decides to qualify the patient for optimization using an alternative test if the test cannot reliably sense cardiac activity in response to the delivered energy in the other ventricle due to a prolonged interventricular conduction condition.

7. The method of claim 1 wherein the algorithm requires regular atrial activity.

8. The method of claim 7 wherein the deciding decides not to qualify the patient for optimization if the patient information indicates irregular atrial activity.

9. The method of claim 7 wherein the deciding decides to qualify the patient for optimization using a specialized algorithm that accounts for irregular atrial activity.

10. The method of claim 9 wherein the specialized algorithm comprises a discrimination technique for sensing cardiac activity in one ventricle responsive to energy delivered to the other ventricle.

* * * * *